US011737952B2

(12) United States Patent
Komann et al.

(10) Patent No.: US 11,737,952 B2
(45) Date of Patent: Aug. 29, 2023

(54) HOLDING DEVICE FOR HOLDING A PLURALITY OF CONTAINERS IN A POSITIVE FIT WHICH IS ESTABLISHED BY A DISPLACEMENT MOVEMENT

(71) Applicant: SCHOTT Pharma Schweiz AG, St. Gallen (CH)

(72) Inventors: Christian Komann, Speicher (CH); Patrick Wolf, St. Gallen (CH); Sandro Kundert, St. Gallen (CH)

(73) Assignee: Schott Pharma Schweiz AG, St. Gallen (CH)

( * ) Notice: Subject to any disclaimer, the term of this patent is extended or adjusted under 35 U.S.C. 154(b) by 195 days.

(21) Appl. No.: 17/153,224

(22) Filed: Jan. 20, 2021

(65) Prior Publication Data
US 2021/0220221 A1    Jul. 22, 2021

(30) Foreign Application Priority Data
Jan. 20, 2020  (EP) .................................... 20152734

(51) Int. Cl.
*B65D 25/10*    (2006.01)
*A61J 1/16*    (2023.01)
(Continued)

(52) U.S. Cl.
CPC . *A61J 1/16* (2013.01); *A61J 1/06* (2013.01); *A61M 5/178* (2013.01); *A61M 5/20* (2013.01); *B65D 25/10* (2013.01)

(58) Field of Classification Search
CPC ....... B01L 9/06; B65D 25/108; B65D 25/101; A61J 1/16; A61J 1/06; B65B 21/18; A61M 5/20; A61M 5/178
(Continued)

(56) References Cited

U.S. PATENT DOCUMENTS 5,080,232 A * 1/1992 Leoncavallo ............. B01L 9/06
                                                   211/74
5,452,810 A    9/1995 Schwartz
(Continued)

FOREIGN PATENT DOCUMENTS

WO    2018020505    2/2018

OTHER PUBLICATIONS

Section 3.2.1 of the European Pharmacopoeia, 7th edition from 2011.
(Continued)

*Primary Examiner* — King M Chu
(74) *Attorney, Agent, or Firm* — Ruggiero McAllister & McMahon LLC

(57) ABSTRACT

A holding device is provided that has a base body having a plurality of openings in a first surface and a plurality of holding elements each having a movable surface. The plurality of holding elements are arranged with respect to the plurality of openings, respectively, such that a container extending in a respective opening of the plurality of openings is held by a respective one of the plurality of holding elements in a positive fit. The movable surface faces the container in a direction that is perpendicular to a height of the container. The holding element establishes the positive fit by a displacement movement of the movable surface. The displacement movement has a direction of movement that inclines an angle with the height of the container in a range from 60 to 120°.

18 Claims, 19 Drawing Sheets

(51) Int. Cl.
  *A61J 1/06*    (2006.01)
  *A61M 5/178*   (2006.01)
  *A61M 5/20*    (2006.01)

(58) Field of Classification Search
  USPC .................................. 211/74; 206/443, 446
  See application file for complete search history.

(56) References Cited

U.S. PATENT DOCUMENTS

2013/0186793 A1\* 7/2013 Gagnieux ............. A61M 5/002
  206/364
2015/0108034 A1\* 4/2015 Deutschle ................ B01L 9/06
  206/593
2016/0130022 A1  5/2016 Wissner

OTHER PUBLICATIONS

DIN ISO 8362-1.
DIN ISO 9187-1.
DIN ISO 110 4 0-4.
DIN ISO 13926-1.
DIN ISO 11040-1.

\* cited by examiner

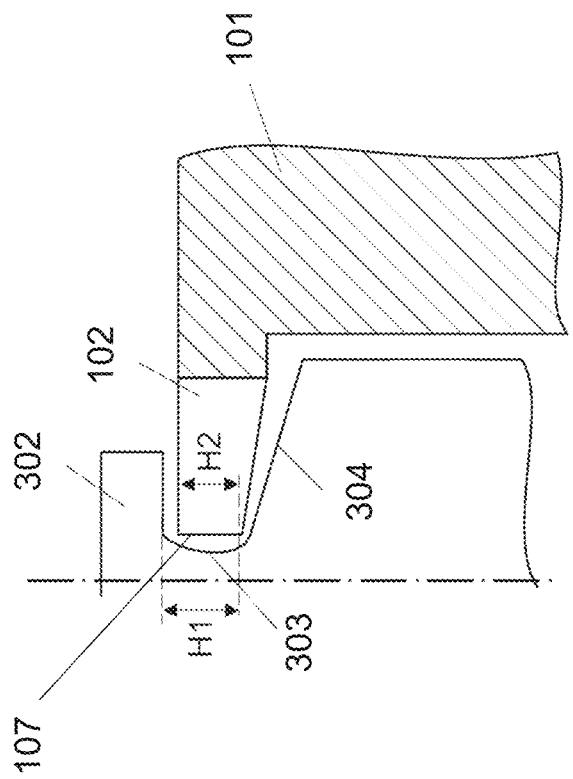
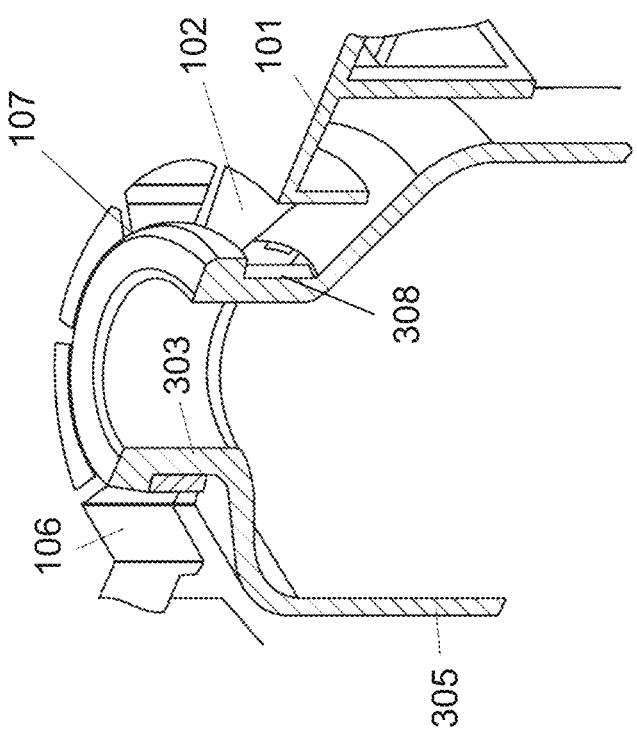

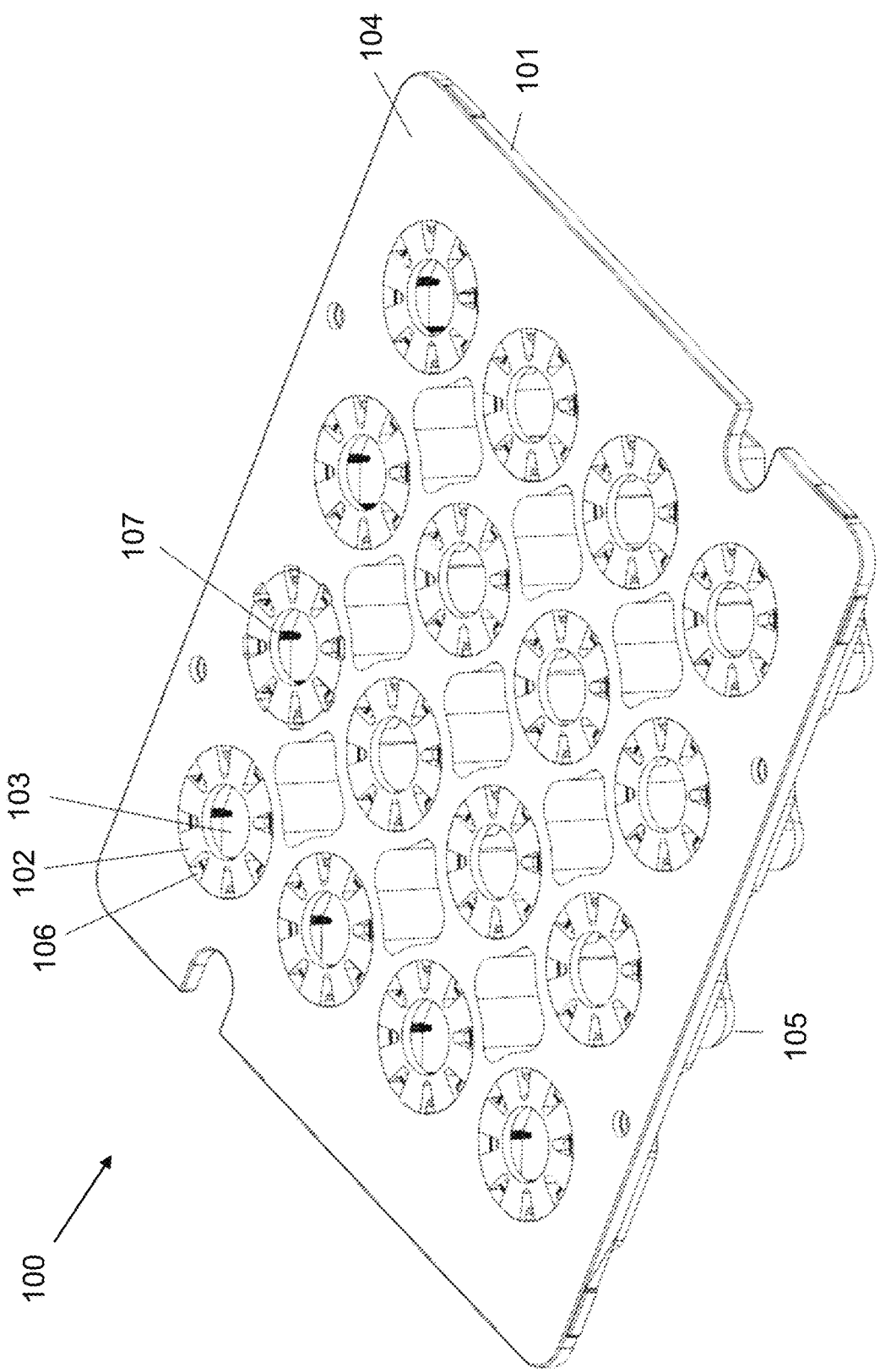

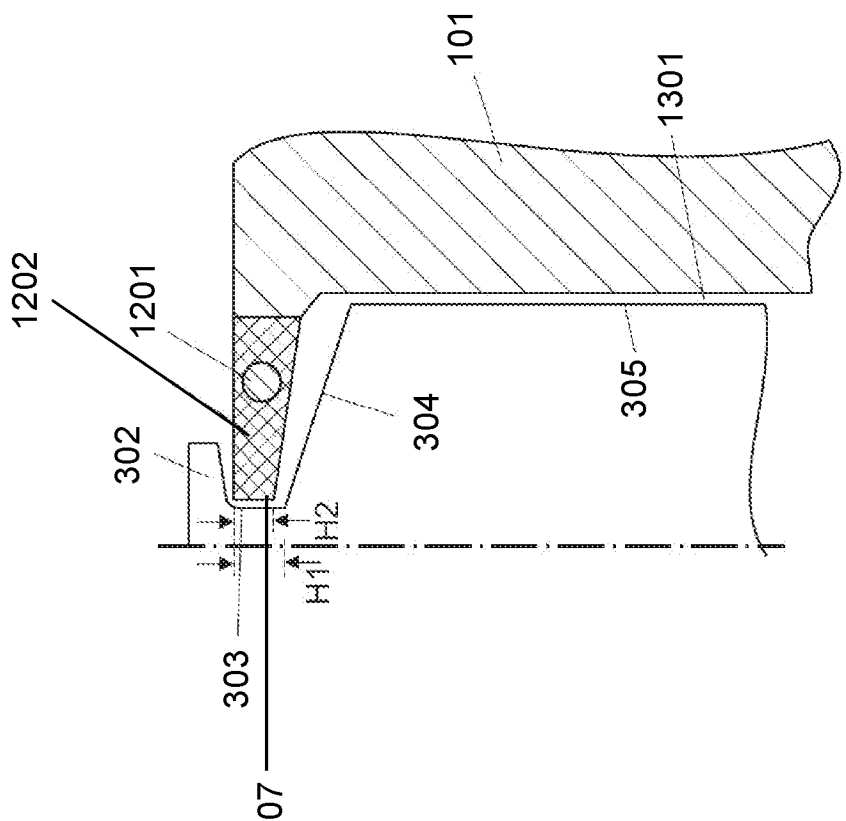
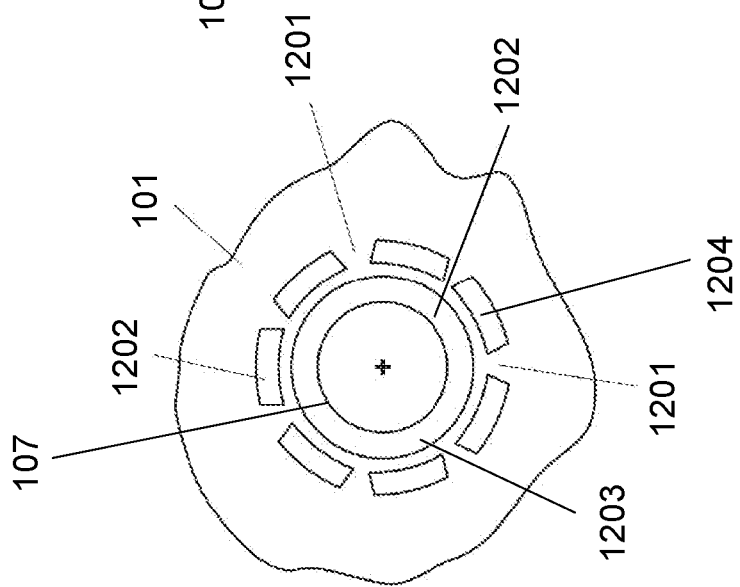
FIG. 13b
FIG. 13a

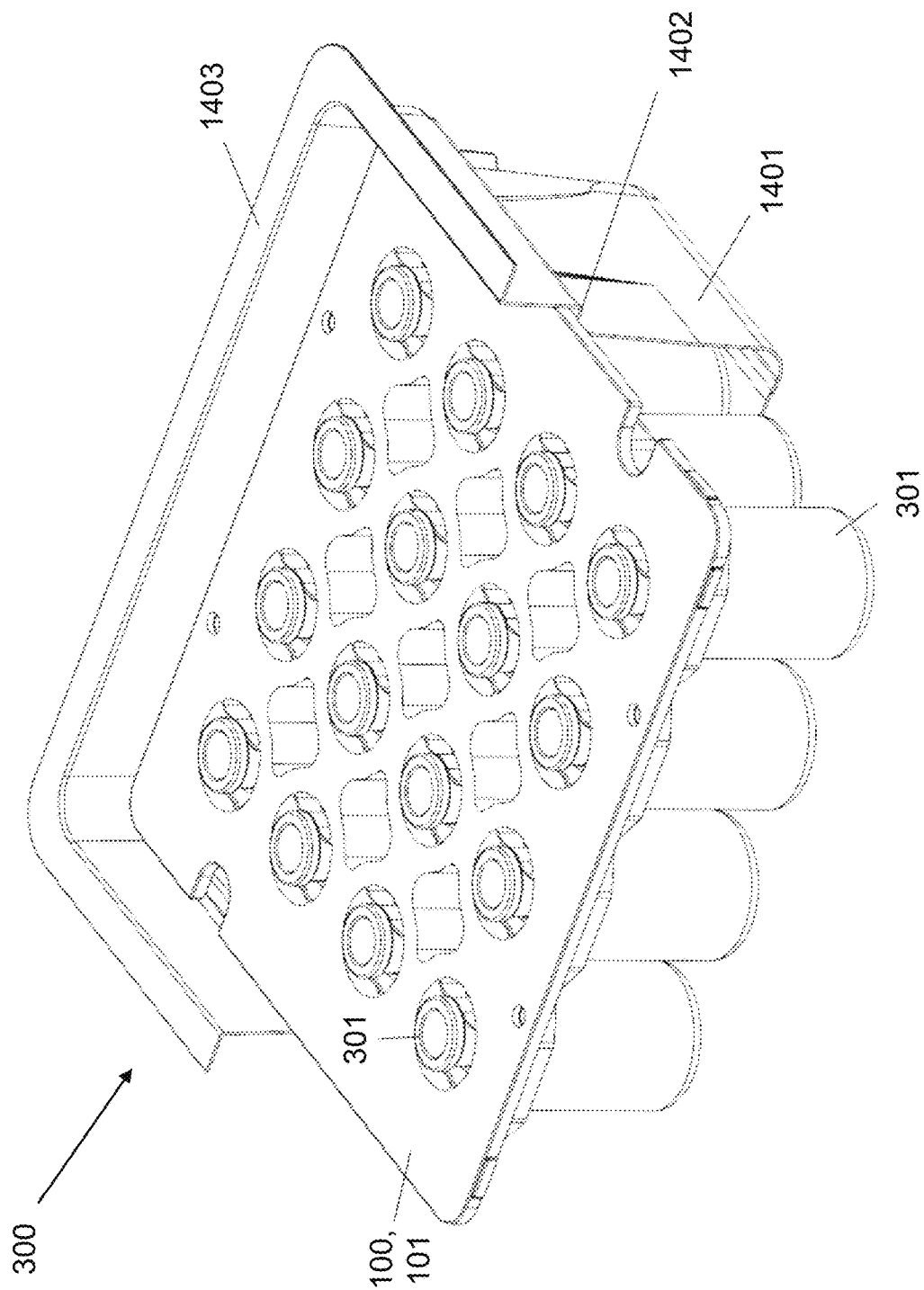

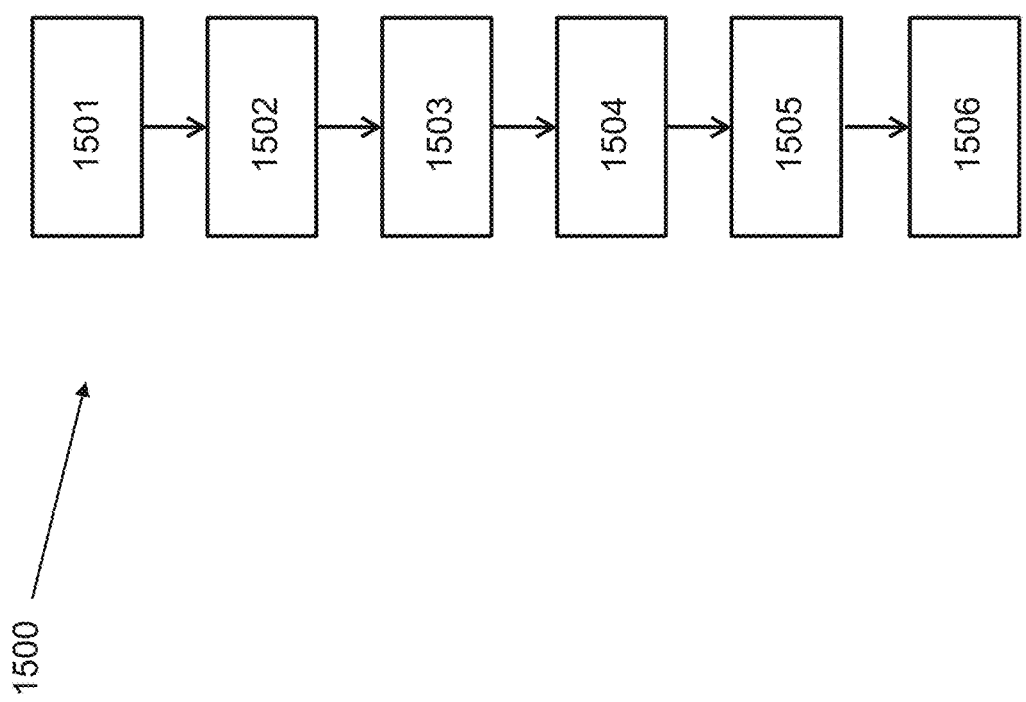

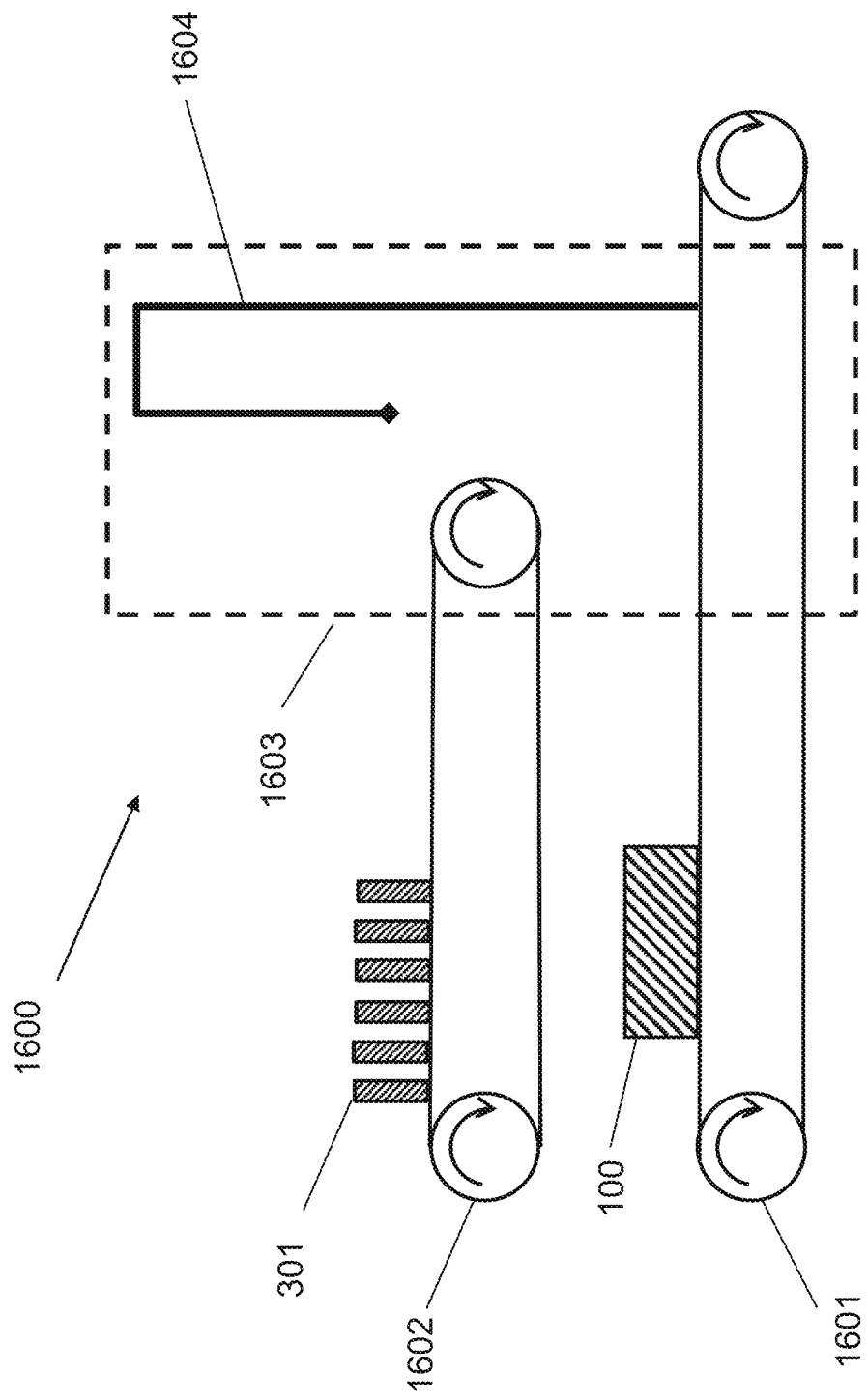

HOLDING DEVICE FOR HOLDING A PLURALITY OF CONTAINERS IN A POSITIVE FIT WHICH IS ESTABLISHED BY A DISPLACEMENT MOVEMENT

CROSS REFERENCE TO RELATED APPLICATIONS

This application claims benefit under 35 USC § 119 of European Application No. 20152734.8 filed Jan. 20, 2020, the entire contents of which are incorporated herein by reference.

BACKGROUND

1. Field of the Invention

The present application relates to a holding device for containers. More particularly, the present application relates to a holding device for containers using in a positive fit established by a displacement movement.

2. Description of Related Art

Containers made from glass have been applied for transporting fluids and powders safely since several centuries. In the last decades, the arts in which glass containers are used for transporting fluids and powders have become increasingly diverse and sophisticated. One such art is the technical field of the present application: pharmaceutical packaging. In the pharmaceutical industry, glass containers—such as vials, syringes, ampoules and cartridges—are applied as primary packaging for all kinds of pharmaceutically relevant compositions, in particular drugs, such as vaccines, and also for cosmetical compositions, in particular cosmetical compositions which are to be injected into the skin.

In the processing of containers for use in pharmaceutical or cosmetical applications, generally so-called nested solutions are preferred nowadays, where a holding structure for containers (also referred to as nest) is used for concurrently holding or supporting a plurality of containers in a given configuration. The nests are usually delivered to a customer, such as a pharmaceutical company or filler, sterile packaged in a transport or packaging container (also referred to as tub). For further processing the containers, the tubs are opened under sterile conditions, e.g., in a clean room. Further processing may take place either with the nest still accommodated in the tub, after removal of the nest of the tub, or after removal of the individual containers from the nest. Further processing the containers often includes steps of sterilizing the containers by irradiation (X-rays or gamma rays) or contact to steam or hydrogen peroxide, filling the containers with a composition, e.g., a pharmaceutical or cosmetical composition, increasing the shelf life of the composition, and sealing the pre-filled containers with lids, stoppers, plungers or the like. After the further processing, the containers may be packaged for retail.

Many active ingredients in pharmaceuticals cannot be kept for long in aqueous solutions. They decompose by hydrolysis within weeks, days, sometimes even hours, so that they are no longer fully effective if they are to be applied to the patient. This is a particular problem for injection or infusion solutions. Therefore, the above further processing of the pre-filled containers includes a treatment for increasing the shelf life which is freeze-drying (also referred to as lyophilization). The pharmaceutical or cosmetical composition is manufactured in liquid form, filtered sterilely, filled into one of the above-mentioned containers and then lyophilized.

The lyophilization technique is a gentle method of removing water from the prepared and filled solution without changing its chemical properties. After sterile filling, the product is placed in a freeze dryer where it is frozen. This is done by cooling the container bottoms, usually at −45 or −50° C., in all cases below the freezing point of the substance mixture. The freezing process is a very important step and significantly influences the subsequent physical structure of the product. After complete freezing of the product, a vacuum is applied in the freezing dryer chamber. If the container bottoms are then heated, the ice begins to sublime, i.e., to pass into the gas phase. The steam can leave the container and precipitates as ice on the ice condenser which is cold at −70 to −80° C. In the end, a so-called cake of active ingredient and often auxiliary substances (for pH value adjustment, as a stabilizing or preserving agent) remains in the vial, which can be stored in a stable manner for several years almost free of water. In essence, the lyophilization technique requires easy access to the container bottoms.

In the prior art, generally two different types of the above nests are known: the cup-nest and the clip-nest. In the clip-nest, necked containers are held by a positive fit at their rolled edge, i.e., at the wider upper rim which adjacent to a narrower neck portion. This positive fit is provided by elastically deformable holding arms, the so-called clips. In the cup-nest, the containers are accommodated inside a cup-like receptacle that encloses the bodies and bottoms of the containers. These nests of the prior art have turned out to be not ideal in terms of further processing containers held by these nests.

SUMMARY

In general, it is an object of the present invention to at least partly overcome a disadvantage arising from the prior art.

It is a further object of the invention to provide a holding device for holding a plurality of pharmaceutical or cosmetical packaging containers, wherein the holding device is particularly suitable for holding the containers while the containers are, one after the other, thoroughly sterilise, filled, lyophilised and closed, preferably by crimping. It is a further object of the invention to provide a holding device for holding a plurality of pharmaceutical or cosmetical packaging containers, wherein this holding device can be reused as often as possible. According to a further object of the invention, a holding device for holding a plurality of pharmaceutical or cosmetical packaging containers is provided, wherein the holding device is particularly suitable for being recycled. According to yet a further object of the invention, a holding device for holding a plurality of pharmaceutical or cosmetical packaging containers is provided, wherein production of this holding is as simple as possible.

It is a further object of the invention to provide an arrangement, including a holding device and a plurality of pharmaceutical or cosmetical packaging containers held by the holding device, wherein the arrangement is suitable for, one after the other, thoroughly sterilising, filling, lyophilising and closing the containers, preferably by crimping, while the containers are held by the holding device. According to a further object of the invention an arrangement, including a holding device and a plurality of pharmaceutical or cosmetical packaging containers held by the holding device, is provided, wherein the containers can be removed from the holding device and inserted back as often as possible without breakage of any part of the holding device. According to a further object of the invention an arrangement, including a holding device and a plurality of pharmaceutical or cosmetical packaging containers held by the holding device, is provided, wherein the holding device is particularly suitable for being recycled. According to yet a further object of the invention an arrangement, including a holding device and a plurality of pharmaceutical or cosmetical packaging containers held by the holding device, is provided, wherein production of this holding is as simple as possible.

Further, in the above, the holding device is, preferably, suitable for being loaded with the containers as quick and simple as possible. Preferably, an empty weight of the above holding devices is as small as possible. Further, a structure of the above holding devices is, preferably, as simple as possible.

According to a further object of the invention, an apparatus is provided which is suitable for loading one of the above advantageous holding devices with containers or for preparing one of the above advantageous arrangements.

A contribution to solving at least one of the objects of the invention is made by an embodiment 1 of a holding device, comprising a base body, and a plurality of holding elements which are arranged at the base body; wherein the base body comprises a plurality of openings in a first surface; wherein for each opening of the plurality of openings at least one holding element of the plurality of holding elements is designed and arranged to hold a container, which extends at least through the first surface into this opening, in a positive fit; wherein in a direction which is perpendicular to a height of the container, which is held by the at least one holding element in the positive fit, a movable surface of the at least one holding element faces the container; wherein the holding device is designed and arranged such that establishing the positive fit includes displacing the movable surface of the at least one holding element, preferably exclusively, by a displacement movement; wherein a direction of the displacement movement inclines an angle with the height of the container, based on the container being held by the at least one holding element in the positive fit, in the range from 60 to 120°, preferably from 70 to 110°, more preferably from 80 to 100, even more preferably from 85 to 95°, most preferably from 88 to 92°. In the preceding, the container, preferably, extends at least through the first surface into the opening with a top region of the container. Preferably, the first surface extends in directions of a width and a length of the base body. A preferred holding device is sterile. A preferred holding device is designed and arranged such that the direction of the displacement movement lies in a plane which is perpendicular to a height of the container, based on the container being held by the at least one holding element in the positive fit. Preferably, in the direction which is perpendicular to the height of the container, which is held by the at least one holding element in the positive fit, the movable surface of the at least one holding element faces a holding region of the container. The plurality of openings, preferably, consists of 4 to 100, more preferably 4 to 90, more preferably 9 to 80, more preferably 12 to 70, even more preferably 12 to 60, most preferably 16 to 50, openings.

In an embodiment 2 of the holding device according to the invention, the holding device is designed according to its embodiment 1, wherein the displacement movement is a translational movement or rotational movement or both.

In an embodiment 3 of the holding device according to the invention, the holding device is designed according to its embodiment 1 or 2, wherein the base body comprises a further surface which is opposite to the first surface, wherein each opening of the plurality of openings extends from the first surface to the further surface. Preferably, the further surface extends in directions of a width and a length of the base body.

In an embodiment 4 of the holding device according to the invention, the holding device is designed according to its embodiment 3, wherein for each opening of the plurality of openings at least one holding element of the plurality of holding elements is designed and arranged to hold a container, which extends via this opening through the first surface and the further surface, in a positive fit.

In an embodiment 5 of the holding device according to the invention, the holding device is designed according to any of its preceding embodiments, wherein the first surface is a planar surface. Additionally or alternatively preferred, the further surface is a planar surface. Preferably, the first and further surfaces are plan-parallel to one another.

According to a preferred embodiment, for each of the holding elements, a surface of the holding element which is on a side of the first surface is planar. Additionally or alternatively preferred, a surface of the holding element which is on a side of the further surface is planar. Additionally or alternatively preferred, one or both of the preceding surfaces of the holding element are parallel to the first or further surface. This design reduces radial force components that tend to further flex the holding elements of the respective opening and push them apart from each other as result of loads acting on a container in a direction of its height.

In an embodiment 6 of the holding device according to the invention, the holding device is designed according to any of its preceding embodiments, wherein in each opening of the plurality of openings, at least part of at least one holding element of the plurality of holding elements is arranged.

In an embodiment 7 of the holding device according to the invention, the holding device is designed according to its embodiment 6, wherein the movable surface of the holding element, at least part of which is arranged in a respective opening, does not protrude from the opening beyond the first surface, or the further surface, or each of both. It is preferred that the movable surface of the holding element, at least part of which is arranged in a respective opening, does not protrude from the opening beyond an upper surface of the base body.

In an embodiment 8 of the holding device according to the invention, the holding device is designed according to any of its preceding embodiments, wherein the holding device is designed and arranged such that the displacement movement can be effected, preferably is to be effected, by at least one actuating tool exerting a displacement force on the at least one holding element. The actuating force is, preferably, directed in the direction of the displacement movement or in a direction which inclines an angle with the height of the container, based on the container being held by the at least one holding element in the positive fit, in the range from 0 to 30°, preferably from 0 to 20°, more preferably from 0 to 10°, even more preferably from 0 to 5°, most preferably from 0 to 3° of the height of the container. A preferred actuating tool comprises, preferably is, a closure for a container of the plurality of containers.

In an embodiment 9 of the holding device according to the invention, the holding device is designed according to any of its preceding embodiments, wherein the positive fit limits a movement of the container, which is held by at least one holding element in the positive fit, in a direction which is parallel to a height of the container, or in a direction which inclines an angle in a range from 80 to 100°, preferably from 85 to 95°, with the first surface, in all directions within a plane which is perpendicular to the height of the container, or a combination of at least two from A. to C.

Preferably, the at least one holding element of each opening is further designed and arranged to form the positive fit with a top region, more preferably a flange, of the container.

In an embodiment 10 of the holding device according to the invention, the holding device is designed according to any of its preceding embodiments, wherein the holding device is designed and arranged such that establishing the positive fit includes elastically deforming, also referred to as flexing, the at least one holding element. Here, the at least one holding element may remain elastically deformed once the positive fit has been established or not.

In an embodiment 11 of the holding device according to the invention, the holding device is designed according to any of its preceding embodiments, wherein for each opening of the plurality of openings a container which extends at least through the first surface into this opening and is held by at least one holding element is not covered by any part of the holding device in a top view onto the container, or in a bottom view onto the container, or both. If a bottom region of the container held by the holding device is accessible, the holding device of the present invention can be used for various kinds of processing, including a freeze-drying (lyophilization) of the containers while being held by the holding device.

In an embodiment 12 of the holding device according to the invention, the holding device is designed according to any of its embodiments 3 to 10, wherein the first surface and the further surface incline an angle of less than 30°, preferably less than 20°, more preferably less than 10°, more preferably less than 5°, even more preferably less than 3°. Most preferably, the first surface is parallel to the further surface.

In an embodiment 13 of the holding device according to the invention, the holding device is designed according to any of its preceding embodiments, wherein the movable surface of the at least one holding element of each opening at least partially encloses a holding area, wherein for each opening a ratio of the holding area of the at least one holding element of this opening to a total opening area of the opening is in a range from 0.01 to 0.95, preferably from 0.02 to 0.92, more preferably from 0.03 to 0.91, more preferably from 0.04 to 0.9, more preferably from 0.05 to 0.8, more preferably from 0.06 to 0.7, more preferably from 0.07 to 0.6, more preferably from 0.08 to 0.5, more preferably from 0.08 to 0.4, more preferably from 0.08 to 0.3, even more preferably from 0.08 to 0.2, most preferably from 0.08 to 0.15.

A preferred holding area is a circular area. Preferably, the movable surface of the at least one holding element of each opening at least partially encloses a holding area in a basic configuration of the at least one holding element. Herein, the basic configuration of the at least one holding element is referred to as a configuration which the at least one holding element assumes if no external force acts on the at least one holding element. Preferably, the at least one holding element is not elastically deformed in its basic configuration. Additionally or alternatively preferred, the at least one holding element does not hold any container in its basic configuration.

In an embodiment 14 of the holding device according to the invention, the holding device is designed according to any of its preceding embodiments, wherein for each opening of the plurality of openings at least 2 holding elements, preferably at least 3 holding elements, more preferably at least 4 holding elements, more preferably at least 5 holding elements, more preferably at least 6 holding elements, even more preferably at least 7 holding elements, most preferably at least 8 holding elements, of the plurality of holding elements are designed and arranged to hold the container, which extends at least through the first surface into this opening, in the positive fit. Preferably, the holding elements of each opening are disposed equidistantly in a direction of a circumference of the opening.

In an embodiment 15 of the holding device according to the invention, the holding device is designed according to any of its preceding embodiments, wherein within a plane in each opening, the at least one holding element of this opening has a curved surface. The plane is, preferably, parallel to an opening area of the opening in the first surface or the further surface or both. Additionally or alternatively preferred, the plane is perpendicular to a height of a container being held by the at least one holding element of the respective opening.

In an embodiment 16 of the holding device according to the invention, the holding device is designed according to any of its any of its preceding embodiments, wherein the movable surface is a curved surface. Preferably, the movable surface is a convexly curved surface with respect to the container, based on the container being held by the at least one holding element in the positive fit.

In an embodiment 17 of the holding device according to the invention, the holding device is designed according to any of its preceding embodiments, wherein the holding device further comprises a plurality of spacer elements, wherein the spacer elements are arranged at the first surface and each of the spacer elements protrudes from the first surface away from the base body, wherein on a side of the first surface which faces away from the base body, between each two neighboring openings of the plurality of openings there is arranged at least part of a spacer element of the plurality of spacer elements. Preferably, each spacer element protrudes from the first surface away from the base body by at least 3 cm, preferably at least 5 cm, more preferably at least 10 cm. Additionally or alternatively preferred, the spacer elements do not protrude more than 20 cm, preferably not more than 15 cm, most preferably most more than 10 cm, from the first surface away from the base body.

In an embodiment 18 of the holding device according to the invention, the holding device is designed according to any of its preceding embodiments, wherein within a plane in each opening, each holding element of this opening extends from its starting point to its end point, wherein the end point is closer to a center of an opening area of the opening than the starting point. The plane is, preferably, parallel to an opening area of the opening in the first surface or the further surface or both. Additionally or alternatively preferred, the plane is perpendicular to a height of a container being held by the at least one holding element of the respective opening. Preferably, the starting point of each holding element is at a lateral surface of the respective opening. A preferred holding element is ribbon-shaped. This design allows to hold a container, which has a rather small diameter in a holding region compared to a diameter of the opening. At the same time, a high stiffness of the holding elements in a direction perpendicular to the plane within the plane (axial direction) can be obtained. The holding elements can, thus, be made very stiff in axial direction, but relatively flexible in within the plane in the opening, thus easing insertion of the containers into the openings.

In an embodiment 19 of the holding device according to the invention, the holding device is designed according to its embodiment 18, wherein within the plane in each opening, each holding element of this opening extends curvilinearly from its starting point to its end point, preferably towards the center of the opening area of the opening.

In an embodiment 20 of the holding device according to the invention, the holding device is designed according to any of its embodiments 1 to 17, wherein within a plane in each opening, each holding element of this opening extends from its starting point to its end point, wherein the starting point and the end point are at a lateral surface of the opening. The plane is, preferably, parallel to an opening area of the opening in the first surface or the further surface or both. Additionally or alternatively preferred, the plane is perpendicular to a height of a container being held by the at least one holding element of the respective opening. A preferred holding element comprises a ribbon-shaped part. A preferred holding element is ribbon-shaped. Preferably, from the starting point to the end point, the holding element extends radially into the opening, i.e., away from the lateral surface of the opening, then it bends towards the lateral surface, then it curves into the opening again, and then it bends towards the lateral surface again which the holding element meets in the second connecting point. Preferably, in a cross section of the respective opening, the web takes the shape of a letter "W" with the bottom of the letter facing towards a lateral center of the opening. In other words, a preferred holding element is bow-shaped. Preferably, a center region of the bow-shaped holding element is bulged radially toward the lateral surface of the opening in an arc-shape. The depression thus formed at the apex of each of the bow-shaped holding elements may further assist the holding elements in snuggly contacting the container to be held. A holding element of this shape can snuggly contact the holding region of a container to be held, and, thus, reliably hold the container even at a rather high container weight. Preferably at least two, more preferably 3, holding elements are disposed along the circumference of the opening, preferably at equidistant spacing. Additionally or alternatively preferred, between the starting and end points of a holding element, the holding element can be elastically deformed towards the lateral surface of the opening. The preceding design of the holding elements is particularly suitable to reduce high tension peaks caused conventionally by rather small contact regions between a holding region of a container and a holding element. At the same time, the design allows to elastically deform the holding elements by applying a rather small force to an extent which allows easy insertion of a container into the respective opening.

According to a further preferred embodiment each of the holding elements forms a closed loop with part of the lateral surface of the respective opening between the starting and end points of the holding element. Here, an arc formed by the lateral surface between the starting and end points of the holding element amounts, preferably, to less than half of a circumference of the lateral surface. In case of a circular segment, the arc spans, preferably, less than 180° of a circle. This design allows a relatively wide contact region between the holding region of the container and the holding element. This further promotes reduction of high-tension peaks.

According to a further embodiment an actuating flap is formed on a side of each of the holding elements facing the lateral surface of the opening. The actuating flap allows to easily apply an actuating tool for actuating the displacement movement of the holding element for insertion of a container into the opening or removal thereof.

According to a further embodiment a width of each of the ribbon-shaped holding elements in radial direction is constant and wherein a lower end of each of the holding elements is wedge-shaped. The holding elements generally may have a rectangular cross-section, which enables a high stiffness in axial direction and at the same time a uniform, homogenous transfer of forces through the holding element even if high loads are exerted on the containers in axial direction.

In an embodiment 21 of the holding device according to the invention, the holding device is designed according to its embodiment 20, wherein within the plane in each opening, for each holding element, there is a gap between a circumference of this opening and the holding element.

In an embodiment 22 of the holding device according to the invention, the holding device is designed according to any of its embodiments 1 to 17, wherein the at least one holding element of each opening comprises a first part, and a second part, wherein within a plane in the opening each of the first part and the second part at least partially, preferably fully, surrounds a center of the opening, wherein the first part is harder than the second part. Preferably, the first part has a first shore A hardness, wherein the second part has a second A shore hardness, wherein the first shore A hardness is more than the second shore A hardness. A preferred second part is ring-shaped. A preferred first part is of a shape of a, preferably continuous, ring. Preferably, the first part is embedded in the second part. Preferably, the second shore A hardness is in the range from 20 to 100, more preferably from 20 to less than 100, more preferably from 30 to 90, even more preferably from 20 to less than 90. Additionally or alternatively preferred, the first shore A hardness is at least 80, more preferably at least 90, more preferably more than 90, more preferably at least 100, even more preferably more than 100.

According to a further embodiment the holding elements are formed as webs protruding radially inward into the openings, wherein the webs of each opening together form an integral holding ring with a central opening for holding the containers, each web being formed of a plastic material and including a resilient inlay, preferably made of a thermoplastic elastomer, so that a width of the central opening can be increased by compressing the resilient inlay, for insertion of a container into the central opening. Here, the integral holding ring can be designed to firmly support or even clamp the containers. By providing an inlay of a different material in the webs that can be compressed easily, the webs can be deformed easily in radial direction, which will result in a radial expansion or broadening of the holding ring to a sufficient extent to enable insertion of a container into the central opening or removal thereof.

In an embodiment 23 of the holding device according to the invention, the holding device is designed according to its embodiment 22, wherein an inner diameter of the first part is more than am inner diameter of the second part. Preferably, the movable surface of the respective holding element is a surface of the second part.

In an embodiment 24 of the holding device according to the invention, the holding device is designed according to its embodiment 22 or 23, wherein the second part comprises a first subpart and a further subpart, wherein the first part is between the first subpart and the further subpart. A preferred, first subpart is of a shape of a, preferably continuous, ring. A preferred further subpart is of a shape of a, preferably discontinuous, ring.

In an embodiment 25 of the holding device according to the invention, the holding device is designed according to its embodiment 24, wherein a diameter of the first subpart is less than a diameter of the further subpart.

In an embodiment 26 of the holding device according to the invention, the holding device is designed according to any of its preceding embodiments, wherein in the direction which is perpendicular to the height of the container, which is held by the at least one holding element in the positive fit, the movable surface of the at least one holding element faces a holding region of the container; wherein an outer surface of the holding region is a cylinder shell surface.

In an embodiment 27 of the holding device according to the invention, the holding device is designed according to any of its preceding embodiments, wherein each of the containers has an interior volume in a range from 0.5 to 100 ml, preferably from 1 to 100 ml, more preferably from 1 to 50 ml, even more preferably from 1 to 10 ml, most preferably from 2 to 10 ml.

In an embodiment 28 of the holding device according to the invention, the holding device is designed according to any of its preceding embodiments, wherein each of the containers comprises a wall, preferably a wall of glass, which at least partially encloses an interior volume, wherein the holding region is a region of a surface of the wall.

In an embodiment 29 of the holding device according to the invention, the holding device is designed according to its embodiment 28, wherein the glass of the wall of glass is of a type selected from the group consisting of a borosilicate glass, preferably a type I glass; an aluminosilicate glass; and fused silica; or of a combination of at least two thereof.

In an embodiment 30 of the holding device according to the invention, the holding device is designed according to its embodiment 28 or 29, wherein the wall comprises from top to bottom of the container a top region; a body region, which follows the top region via a shoulder; and a bottom region, which follows the body region via a heel.

Preferably, the holding region is a region of an outer surface of the top region. Preferably, the body region is a lateral region of the container. Particularly preferable, the body region of the wall forms a hollow cylinder. The top region preferably comprises, more preferably consists of, from top to bottom of the container a flange and a neck. Preferably, the positive fit is between the at least one holding element and a part of the outer surface of the top region, more preferably the flange or the neck or both. Preferably, the neck comprises the holding region. A preferred neck forms a hollow cylinder. Preferably, a ratio of a height H2 of the movable surface of the at least one holding element to a height H1 of the holding region or of the neck or both is larger than 0.5, more preferably larger than 0.6 and even more preferably larger than 0.7.

In an embodiment 31 of the holding device according to the invention, the holding device is designed according to its embodiment 30, wherein throughout the body region a wall thickness of the wall is in a range from ±0.3 mm, preferably ±0.2 mm, more preferably ±0.1 mm, most preferably ±0.08 mm, in each case based on a mean value of the wall thickness in the body region.

In an embodiment 32 of the holding device according to the invention, the holding device is designed according to its embodiment 30 or 31, wherein throughout the body region a wall thickness of the wall is in a range from 0.2 to 5 mm, preferably from 0.4 to 3 mm, more preferably from 0.5 to 2 mm, most preferably from 0.6 to 1.5 mm. In a preferred embodiment throughout the body region a thickness of the wall is in a range from 0.9 to 1.1 mm. In a further preferred embodiment throughout the body region a thickness of the wall is in a range from 1.5 to 1.7 mm.

In an embodiment 33 of the holding device according to the invention, the holding device is designed according to any of its embodiments 28 to 32, wherein towards the interior volume the wall is at least partially superimposed by an alkali metal barrier layer or by a hydrophobic layer or both.

In an embodiment 34 of the holding device according to the invention, the holding device is designed according to any of its preceding embodiments, wherein each of the containers is a packaging container for a pharmaceutical composition or a cosmetical composition or both. Preferably, the container is a primary packaging container for a pharmaceutical composition or a cosmetical composition or both. A preferred pharmaceutical composition is a liquid. A preferred cosmetical composition is a liquid. Preferably, the containers are suitable for packaging parenteralia in accordance with section 3.2.1 of the European Pharmacopoeia, $7^{th}$ edition from 2011.

In an embodiment 35 of the holding device according to the invention, the holding device is designed according to any of its preceding embodiments, wherein the containers of the plurality of containers are one selected from the group consisting of vials, syringes, cartridges, autoinjectors and ampoules; or a combination of at least two thereof. Additionally or alternatively preferred, the containers of the plurality of containers are medical devices, wherein medical devices for parenteral administration, preferably by injection, are preferred. A preferred medical device for parenteral administration by injection is an autoinjector. A preferred autoinjector is an insulin pen.

In an embodiment 36 of the holding device according to the invention, the holding device is designed according to any of its preceding embodiments, wherein in the direction which is perpendicular to the height of the container, which is held by the at least one holding element in the positive fit, the movable surface of the at least one holding element faces a holding region of the container; wherein a part of each of the containers of the plurality of containers, which comprises the holding region, has an outer diameter in the range from 5 to 100 mm, preferably from 5 to 80 mm, more preferably from 5 to 70 mm, more preferably from 5 to 60 mm, more preferably from 5 to 50 mm, more preferably from 5 to 40 mm, preferably from 5 to 35 mm, even more preferably from 5 to 20 mm, most preferably from 10 to 20 mm. For particularly preferred containers, the part of the containers which comprises the holding region, has an outer diameter which is in a range of ±0.35 mm, preferably ±0.25 mm, around a value selected from the group consisting of 5.5 mm, 6.85 mm, 7.2 mm, 7.75 mm, 8.15 mm, 10.5 mm, 10.85 mm, 11.0 mm, 11.4 mm, 11.6 mm, 15.0 mm 16.5 mm, 17.5 mm, 18.0 mm, 21.6 mm, and 31.5 mm. Preferred containers, the part of which comprises the holding region and has an outer diameter which is in a range of ±0.35 mm, preferably ±0.25 mm, around a value selected from the group consisting 10.5 mm, 16.5 mm, and 17.5 mm are vials. Preferred containers, the part of which comprises the holding region and has an outer diameter which is in a range of ±0.35 mm, preferably ±0.25 mm, around a value selected from the group consisting 5.5 mm, 7.2 mm, 7.75 mm, 9.4 mm and 11.0 mm are cartridges. Preferred containers, the part of which comprises the holding region and has an outer diameter which is in a range of ±0.35 mm, preferably ±0.25 mm, around a value selected from the group consisting 6.85 mm, 8.15 mm, 10.85 mm, 11.4 mm, 11.6 mm, 15.0 mm, 18.0 mm, 21.6 mm, and 31.5 mm are syringes.

In an embodiment 37 of the holding device according to the invention, the holding device is designed according to any of its preceding embodiments, wherein a ratio of a sum of the widths of the holding elements along a circumference of a respective opening to the total circumference of a respective opening is less than 0.15, more preferably less than 0.1 and even more preferably less than 0.075. Additionally or alternatively preferred, a ratio of a sum of the widths of the holding elements along a circumference of a respective opening to the total circumference at the same radial position is larger than 0.3, more preferably larger than 0.4 and even more preferably larger than 0.5. The afore-mentioned selective design of the mechanical characteristics of the holding elements thus enables particularly wide or large-area gaps, which may be used as flow paths between the front side and the rear side of the base body, which can efficiently assist in venting, pressure compensation, removal of residual moisture and preventing any condensation during processing of the containers when held at by the holding device that may even be accommodated in a tub or held by a frame in a processing station during processing of the containers.

According to a further embodiment the movable surfaces of all holding elements of a respective opening at least partially surround an inner holding area having an area that basically corresponds to an area of the tubular portion of circular profile of a container to be held in the inner holding area, wherein a ratio of the area of the inner holding area to the total area of a respective opening is less than 0.6, more preferably less than 0.5 and even more preferably less than 0.4. Additionally or alternatively preferred, a ratio of the total area of gaps provided between the holding elements and a lateral surface of the respective opening is larger than 0.7, more preferably larger than 0.75 and even more preferably larger than 0.8. The afore-mentioned selective design of the mechanical characteristics of the holding elements thus enables particularly wide or large-area gaps, which may be used as flow paths between the front side and the rear side of the carrier, which can efficiently assist in venting, pressure compensation, removal of residual moisture and preventing any condensation during processing of the containers when held by the holding device that may even be accommodated in a tub or held by a frame in a processing station during processing of the containers.

A contribution to solving at least one of the objects of the invention is made by an embodiment 1 of a process 1, comprising as process step (a) providing a holding device, comprising a base body, comprising a plurality of openings in a first surface, and a plurality of holding elements which are arranged at the base body, and a plurality of containers; and (b) inserting each of the containers of the plurality of containers into one of the openings of the plurality of openings so that each container extends at least through the first surface into the respective opening, and is held by at least one holding element of the plurality of holding elements in a positive fit; wherein in a direction which is perpendicular to a height of the container, which is held by the at least one holding element in the positive fit, a movable surface of the at least one holding element faces the container; wherein establishing the positive fit in the process step (b) includes displacing the movable surface of the at least one holding element, preferably exclusively, by a displacement movement; wherein a direction of the displacement movement inclines an angle with the height of the container, based on the container being held by the at least one holding element in the positive fit, in the range from 60 to 120°, preferably from 70 to 110°, more preferably from 80 to 100, even more preferably from 85 to 95°, most preferably from 88 to 92°. The containers are each preferably configured as described in the context of any of the embodiments of the holding device of the invention. The holding device which is provided in step (a), preferably, is the holding device of the invention according to any of its embodiments. Particularly preferably, the displacement movement lies in a plane which is perpendicular to a height of the container, based on the container being held by the at least one holding element in the positive fit.

In an embodiment 2 of the process 1 according to the invention, this process is designed according to its embodiment 1, wherein the displacement movement is a translational movement or rotational movement or both.

In an embodiment 3 of the process 1 according to the invention, this process is designed according to its embodiment 1 or 2, wherein the base body comprises a further surface which is opposite to the first surface, wherein each opening of the plurality of openings extends from the first surface to the further surface, wherein in the process step (b) each of the containers of the plurality of containers is inserted into one of the openings of the plurality of openings so that each container extends via this opening through the first surface and the further surface.

In an embodiment 4 of the process 1 according to the invention, this process is designed according to any of its preceding embodiments, wherein for each of the containers the process step (b) comprises elastically deforming the at least one holding element. Here, the at least one holding element may remain elastically deformed once the positive fit has been established or not.

In an embodiment 5 of the process 1 according to the invention, this process is designed according to any of its preceding embodiments, wherein in the process step (b) the displacement movement is effected by at least one actuating tool exerting a displacement force on the at least one holding element. The actuating force is, preferably, directed in the direction of the displacement movement or in a direction which inclines an angle with the height of the container, based on the container being held by the at least one holding element in the positive fit, in the range from 0 to 30°, preferably from 0 to 20°, more preferably from 0 to 10°, even more preferably from 0 to 5°, most preferably from 0 to 3° of the height of the container.

In an embodiment 6 of the process 1 according to the invention, this process is designed according to any of its preceding embodiments, wherein the process comprises as further process steps (c) placing the holding device with the containers into a packaging container, and (d) closing the packaging container.

A preferred packaging container is a tub.

In an embodiment 7 of the process 1 according to the invention, this process is designed according to its embodiment 6, wherein the process step (d) comprises joining a lid to the packaging container. A preferred lid is a sheet. A preferred sheet is a multilayer sheet. A preferred lid is permeable for an inert gas.

In an embodiment 8 of the process 1 according to the invention, this process is designed according to its embodiment 6 or 7, wherein the process comprises as further process steps (e) placing the packaging container with the holding device and the containers into an outer packaging, and (f) closing the outer packaging.

A preferred outer packaging is a pouch, preferably made from a plastic film. A preferred process step (f) comprises sealing the outer packaging. A preferred outer packaging provides a barrier against a permeation of an inert gas. A preferred outer packaging is hermetically sealed.

In an embodiment 9 of the process 1 according to the invention, this process is designed according to its embodiment 8, wherein prior to the process step (f) an atmosphere in the outer packing is adjusted. Preferably, adjusting the atmosphere in the outer packing comprises introducing an inert gas into the outer packaging. Preferably, the outer packaging is less permeable for the inert gas than the lid. Particularly preferred the outer packing provides a barrier action against a permeation of the inert gas, whereas the lid is permeable for the inert gas.

In an embodiment 10 of the process 1 according to the invention, this process is designed according to any of its preceding embodiments, wherein the process is a process for loading the holding device with the containers.

In an embodiment 11 of the process 1 according to the invention, this process is designed according to any of its preceding embodiments, wherein the process is a process for preparing the arrangement of the invention according to any of its embodiments.

In an embodiment 12 of the process 1 according to the invention, this process is designed according to any of its preceding embodiments, wherein after the process step (b) the process comprises a further process step which comprises treating at least part of an outer surface of each of the containers. Preferably, the treating is conducted prior to the process step (d), more preferably prior to the process step (c).

In an embodiment 13 of the process 1 according to the invention, this process is designed according to its embodiment 12, wherein the treating comprises a sterilization or a lyophilization or both. A preferred sterilization comprises contacting the outer surface with a sterilizing agent or electromagnetic radiation or both. A preferred sterilizing agent is a thermal sterilizing agent or a chemical sterilizing agent or both. A thermal sterilizing agent is designed to sterilize thermally, whereas a chemical sterilizing agent is a chemical which can sterilize upon contact. A preferred thermal sterilizing agent is a hot has, preferably steam. A preferred chemical sterilizing agent is $H_2O_2$. Preferred electromagnetic radiation comprises X-rays or Gamma rays or both.

In an embodiment 14 of the process 1 according to the invention, this process is designed according to any of its preceding embodiments, wherein in the process step (a) the containers are sterile.

In an embodiment 15 of the process 1 according to the invention, this process is designed according to any of its preceding embodiments, wherein the holding device is the holding device according to any of its embodiments.

A contribution to solving at least one of the objects of the invention is made by an embodiment 1 of an arrangement, comprising a holding device, comprising a base body, and a plurality of holding elements which are arranged at the base body, and a plurality of containers; wherein the base body comprises a plurality of openings in a first surface; wherein each of the containers of the plurality of containers extends at least through the first surface into one of the openings, and is held by at least one holding element of the plurality of holding elements in a positive fit; wherein in a direction which is perpendicular to a height of the container a movable surface of the at least one holding element faces the container; wherein the holding device is designed and arranged such that establishing the positive fit includes displacing the movable surface of the at least one holding element, preferably exclusively, by a displacement movement; wherein a direction of the displacement movement inclines an angle with the height of the container, based on the container being held by the at least one holding element in the positive fit, in the range from 60 to 120°, preferably from 70 to 110°, more preferably from 80 to 100, even more preferably from 85 to 95°, most preferably from 88 to 92°. A preferred holding device is designed and arranged such that the direction of the displacement movement lies in a plane which is perpendicular to a height of the container, based on the container being held by the at least one holding element in the positive fit. Preferably, in the direction which is perpendicular to the height of the container, which is held by the at least one holding element in the positive fit, the movable surface of the at least one holding element faces a holding region of the container. The containers are each preferably configured as described in the context of any of the embodiments of the holding device of the invention. The plurality of openings, preferably, consists of 4 to 100, more preferably 4 to 90, more preferably 9 to 80, more preferably 12 to 70, even more preferably 12 to 60, most preferably 16 to 50, openings. Additionally or alternatively preferred, the plurality of containers consists of 4 to 100, more preferably 4 to 90, more preferably 9 to 80, more preferably 12 to 70, even more preferably 12 to 60, most preferably 16 to 50, containers.

In an embodiment 2 of the arrangement according to the invention, this arrangement is designed according to its embodiment 1, wherein the holding device is the holding device of the invention according to any of its embodiments.

In an embodiment 3 of the arrangement according to the invention, this arrangement is designed according to its embodiment 1 or 2, wherein the displacement movement is a translational movement or rotational movement or both.

In an embodiment 4 of the arrangement according to the invention, this arrangement is designed according to any of its embodiments 1 to 3, wherein the base body comprises a further surface which is opposite to the first surface, wherein each opening of the plurality of openings extends from the first surface to the further surface, wherein each container extends via an opening of the plurality of openings through the first surface and the further surface.

In an embodiment 5 of the arrangement according to the invention, this arrangement is designed according to any of its preceding embodiments, wherein at least part, preferably each, of the containers of the plurality of containers is filled with a pharmaceutical composition or a cosmetical composition or both.

In an embodiment 6 of the arrangement according to the invention, this arrangement is designed according to any of its preceding embodiments, wherein for each of the containers of the plurality of containers the respective positive fit limits a movement of the container in a direction selected from a group consisting of parallel to a height of the container, inclined an angle in a range from 80 to 100°, preferably from 85 to 95°, with the first surface, in all directions within a plane which is perpendicular to the height of the container, and any combinations thereof.

In an embodiment 7 of the arrangement according to the invention, this arrangement is designed according to any of its preceding embodiments, wherein the movable surface of the holding element, at least part of which is arranged in a respective opening, does not protrude from the opening beyond the first surface, or the further surface, or each of both.

In an embodiment 8 of the arrangement according to the invention, this arrangement is designed according to any of its preceding embodiments, wherein each of the containers comprises a container opening, wherein none of the container openings is covered by any part of the holding device.

In an embodiment 9 of the arrangement according to the invention, this arrangement is designed according to any of its preceding embodiments, wherein each of the containers comprises a bottom, wherein none of the bottoms is covered by any part of the holding device.

In an embodiment 10 of the arrangement according to the invention, this arrangement is designed according to any of its preceding embodiments, wherein the arrangement further comprises a, preferably closed, packaging container, wherein the holding device and the containers are arranged in the packaging container.

In an embodiment 11 of the arrangement according to the invention, this arrangement is designed according to its embodiment 10, wherein the packaging container is closed by a lid which is joined to the packaging container.

In an embodiment 12 of the arrangement according to the invention, this arrangement is designed according to its embodiment 10 or 11, wherein the arrangement further comprises a, preferably closed, outer packaging, wherein the packaging container is arranged in the outer packaging.

In an embodiment 13 of the arrangement according to the invention, this arrangement is designed according to its embodiment 12, wherein the outer packaging comprises an atmosphere which comprises an inert gas at a proportion of at least 50 vol.-%, preferably at least 60 vol.-%, preferably at least 70 vol.-%, more preferably at least 80 vol.-%, even more preferably at least 90 vol.-%, most preferably at least 95 vol.-%, in each case based on a volume of the atmosphere.

In an embodiment 14 of the arrangement according to the invention, this arrangement is designed according to any of its preceding embodiments, wherein the containers are sterile. Preferably, the arrangement is sterile.

In an embodiment 15 of the arrangement according to the invention, this arrangement is designed according to any of its preceding embodiments, wherein the arrangement is obtainable by the process 1 according to any of its embodiments.

A contribution to solving at least one of the objects of the invention is made by an embodiment 1 of an apparatus, comprising as components a holding device feed, a container feed, and a loading station, wherein the holding device feed is designed and arranged to feed a holding device to the loading station, wherein the holding device comprises a base body, comprising a plurality of openings in a first surface, and a plurality of holding elements which are arranged at the base body, wherein the container feed is designed and arranged to feed a plurality of containers to the loading station, wherein the loading station is designed and arranged to insert each of the containers of the plurality of containers into one of the openings of the plurality of openings so that each container extends at least through the first surface into this opening, and is held by at least one holding element of the plurality of holding elements in a positive fit; wherein in a direction which is perpendicular to a height of the container, which is held by the at least one holding element in the positive fit, a movable surface of the at least one holding element faces the container; wherein establishing the positive fit includes displacing the movable surface of the at least one holding element, preferably exclusively, by a displacement movement; wherein a direction of the displacement movement inclines an angle with the height of the container, based on the container being held by the at least one holding element in the positive fit, in the range from 60 to 120°, preferably from 70 to 110°, more preferably from 80 to 100, even more preferably from 85 to 95°, most preferably from 88 to 92°. The containers are each preferably configured as described in the context of any of the embodiments of the holding device of the invention. Preferably, a volume of the apparatus which contains the loading station is sterile. The holding device, preferably, is the holding device of the invention according to any of its embodiments. Particularly preferably, the displacement movement lies in a plane which is perpendicular to a height of the container, based on the container being held by the at least one holding element in the positive fit. Preferably, the loading station is designed and arranged to establish the positive fit by inserting the container of the plurality of containers into the respective opening of the plurality of openings.

In an embodiment 2 of the apparatus according to the invention, this apparatus is designed according to its embodiment 1, wherein the displacement movement is a translational movement or rotational movement or both.

In an embodiment 3 of the apparatus according to the invention, this apparatus is designed according to its embodiment 1 or 2, wherein the base body comprises a further surface which is opposite to the first surface, wherein each opening of the plurality of openings extends from the first surface to the further surface, wherein the loading station is designed and arranged to insert each of the containers of the plurality of containers into one of the openings of the plurality of openings so that each container extends via this opening through the first surface and the further surface.

In an embodiment 4 of the apparatus according to the invention, this apparatus is designed according to any of its preceding embodiments, wherein the loading station is further designed and arranged for converting the at least one holding element from a basic configuration to an insertion configuration prior to inserting the container.

In an embodiment 5 of the apparatus according to the invention, this apparatus is designed according to its embodiment 4, wherein converting the at least one holding element from its basic configuration to its insertion configuration includes elastically deforming the at least one holding element.

In an embodiment 6 of the apparatus according to the invention, this apparatus is designed according to its embodiment 4 or 5, wherein converting the at least one holding element from its basic configuration to its insertion configuration includes the displacement movement.

In an embodiment 7 of the apparatus according to the invention, this apparatus is designed according to any of its preceding embodiments, wherein the apparatus further comprises a packaging container feed and a first packaging station, wherein the packaging container feed is designed and arranged to feed a packaging container to the first packaging station, wherein the first packaging station is designed and arranged for placing the holding device, preferably with the plurality of containers, into the packaging container and for subsequently closing the packaging container, thereby obtaining a closed packaging container. Preferably, the first packaging station is arranged downstream of the loading station.

In an embodiment 8 of the apparatus according to the invention, this apparatus is designed according to any of its preceding embodiments, wherein the apparatus further comprises an outer packaging feed and a further packaging station, wherein the outer packaging feed is designed and arranged to feed an outer packaging feed to the further packaging station, wherein the further packaging station is designed and arranged for placing the closed packaging container into the outer packaging and for closing the outer packaging. Preferably, the further packaging station is arranged downstream of the first packaging station.

In an embodiment 9 of the apparatus according to the invention, this apparatus is designed according to its embodiment 8, wherein the apparatus further comprises a gas feed which is designed and arranged to introduce an inert gas into the outer packaging prior to the outer packaging being closed by the further packaging station.

In an embodiment 10 of the apparatus according to the invention, this apparatus is designed according to any of its preceding embodiments, wherein the apparatus further comprises a treatment station which is designed and arranged to treat at least part of an outer surface of each of the containers after the containers have been inserted into the openings, preferably prior to closing the packaging container. Preferably, the treatment station is arranged downstream of the loading station or upstream of the first packaging station or both. Preferably, the treating comprises a sterilization or a lyophilization or both.

In an embodiment 11 of the apparatus according to the invention, this apparatus is designed according to any of its preceding embodiments, wherein the holding device is the holding device of the invention according to any of its embodiments.

In an embodiment 12 of the apparatus according to the invention, this apparatus is designed according to any of its preceding embodiments, wherein the apparatus is designed for conducting the process 1 of the invention according to any of its embodiments.

In an embodiment 13 of the apparatus according to the invention, this apparatus is designed according to any of its preceding embodiments, wherein the apparatus is designed for preparing the arrangement of the invention according to any of its embodiments.

A contribution to solving at least one of the objects of the invention is made by an embodiment 1 of a process 2, comprising as process steps (a) providing the arrangement of the invention according to any of its embodiments; (b) filling at least part of the containers with a pharmaceutical composition or a cosmetical composition or both.

In a preferred embodiment, the process 2 of the invention comprises a process step (c) closing each of the at least part of the containers with a closure.

Preferably, process step (c) comprises effecting the displacement movement or a movement which opposite the displacement movement, preferably by an actuating tool which comprises, preferably is, the closure.

In an embodiment 2 of the process 2 according to the invention, this process is designed according to its embodiment 1, wherein prior to the process step (b) the packaging container is opened.

In an embodiment 3 of the process 2 according to the invention, this process is designed according to its embodiment 1 or 2, wherein prior to the process step (b) the holding device is removed from the packaging container. Preferably, in the process step (b), the containers are held by the holding device.

In an embodiment 4 of the process 2 according to the invention, this process is designed according to any of its embodiments 1 to 3, wherein prior to the process step (b) the containers are removed from the packaging container. Preferably, in the described step, the holding device is not removed from the packaging container.

In an embodiment 5 of the process 2 according to the invention, this process is designed according to any of its preceding embodiments, wherein prior to the process step (b) the containers are removed from the holding device.

In an embodiment 6 of the process 2 according to the invention, this process is designed according to any of its preceding embodiments, wherein prior to the process step (b) the outer packaging is opened and the packaging container is removed from the outer packaging.

In an embodiment 7 of the process 2 according to the invention, this process is designed according to any of its preceding embodiments, wherein the process is a process for filling the containers with the pharmaceutical composition or the cosmetical composition or both.

A contribution to solving at least one of the objects of the invention is made by an embodiment 1 of a use 1 of the holding device of the invention according to any of its embodiments for holding a plurality of containers, selected from the group consisting of vials, syringes, cartridges, and ampoules, or a combination of at least two thereof.

A contribution to solving at least one of the objects of the invention is made by an embodiment 1 of a use 2 of a filling machine for filling the containers of the arrangement of the invention according to any of its embodiments with a pharmaceutical composition or a cosmetical composition or both. Therein, the containers are, preferably, held by the holding device as described in the context of the arrangement.

Features described as preferred in one category of the invention, for example according to the holding device, are analogously preferred in an embodiment of the other categories according to the invention such as the arrangement or the process 1.

Base Body

The base body of the holding device may be of any shape or material which the skilled person deems appropriate in the context of the invention. Preferably, the base body is made from a plastic. Additionally or alternatively preferred, the base body has a shore A hardness of at least 80, more preferably at least 90, more preferably more than 90, more preferably at least 100, even more preferably more than 100. Additionally or alternatively preferred, the base body is of a plate-like shape. Preferably, a width and a length of the base body are each at least 3 times, more preferably at least 5 times, even more preferably at least 10 times, most preferably at least 20 times, a thickens of the base body. The plurality of openings, preferably, consists of 4 to 100, more preferably 4 to 90, more preferably 9 to 80, more preferably 12 to 70, even more preferably 12 to 60, most preferably 16 to 50, openings. Additionally or alternatively preferred, the holding device of the inventions is, preferably, configured for holding 4 to 100, more preferably 4 to 90, more preferably 9 to 80, more preferably 12 to 70, even more preferably 12 to 60, most preferably 16 to 50, containers. Further, the openings of the plurality of openings in the first surface may be any kind of opening which the skilled person deems appropriate to accommodate the containers such that they can be held by the holding elements. A preferred opening is a recess or a through-hole, wherein the through-hole is particularly preferred. A preferred through-hole has a circular cross section. A particularly preferred through-hole is of a cylindrical shape. This means that a lateral surface of the through-hole is a cylinder shell surface. Additionally or alternatively preferred, the openings are arranged at the first surface in a regular pattern, preferably in an array which consists of rows and columns which are, preferably, perpendicular to one another.

Holding Elements

The holding elements of the holding device may be of any shape or material which the skilled person deems appropriate in the context of the invention, in particular for holding the containers in the positive fit. Preferably, the holding elements are at least in part, preferably as a whole, made from a plastic. A preferred plastic is a thermoplastic elastomer. Additionally or alternatively preferred, the holdings elements are at least partially, preferably as a whole, made from a plastic which is more flexible than a plastic which the base body is made from. The base body is, preferably, made from a thermoset. Further preferred, the holding elements are connected to the base body, preferably directly. In general, the holding elements may be arranged on or in one selected from the group, consisting of on the first surface, on the further surface, and in the openings. A combination of at least two from the preceding group is also conceivable. Preferably, the holding elements are arranged in the openings of the plurality of openings. This means that the holding elements are arranged on a lateral surface of the openings. Here, the holding elements may or may not protrude from the openings beyond the first or further surface, or not. Preferably, the holding elements do not protrude beyond the first surface or the further surface or both. In case, there is of more than one holding element in each opening, these holding elements are, preferably, arranged along a circumference of the opening one after the other, preferably in an equidistant manner. Preferably, at least part of each of the holding elements, more preferably the whole of each of the holding elements, has a shore A hardness in the range from 30 to 80, more preferably from 40 to 70. If only part of each of the holding elements has a shore A hardness in one of the preceding ranges, for each of the openings, these parts, preferably, form the moveable surface.

Container

The container according to the invention may have any size or shape which the skilled person deems appropriate in the context of the invention. Preferably, a top region of the container comprises an opening, which allows for inserting a pharmaceutical composition into the interior volume of the container. In that case, a wall of the container encloses the interior volume of the container only partially. The container is preferably a glass container, a wall of glass of which at least partially encloses an interior volume of the container. Preferably, the wall of glass is of a one-piece design. The wall of glass may preferably be made by blow moulding a glass melt; or by preparing a tube of a glass, preferably in form of a hollow cylinder, forming the bottom of the container from one end of the tube, thereby closing the tube at this end, and forming the top region of the container from the opposite end of the tube. Preferably, the wall of glass is transparent. The holding region of the container is, preferably, a region of an outer surface of the container, more preferably of an outer lateral surface of the container, which, preferably, is a cylinder shell surface.

For the use in this document, the interior volume represents the full volume of the interior of the container. This volume may be determined by filling the interior of the container with water up to the brim and measuring the volume of the amount of water which the interior can take up to the brim. Hence, the interior volume as used herein is not a nominal volume as it is often referred to in the technical field of pharmacy. This nominal volume may for example be less than the interior volume by a factor of about 0.5.

Glass

The wall of glass comprises a glass, more preferably essentially consists of the glass. This glass may be any type of glass and may have any composition which the skilled person deems suitable in the context of the invention. Preferably, the glass is suitable for pharmaceutical packaging. Particularly preferable, the glass is of type I in accordance with the definitions of glass types in section 3.2.1 of the European Pharmacopoeia, $7^{th}$ edition from 2011. Additionally or alternatively preferable to the preceding, the glass is selected from the group consisting of a borosilicate glass, an aluminosilicate glass, and fused silica; or a combination of at least two thereof, wherein an aluminosilicate glass is particularly preferred. For the use in this document, an aluminosilicate glass is a glass which has a content of $Al_2O_3$ of more than 8 wt.-%, preferably more than 9 wt.-%, particularly preferable in a range from 9 to 20 wt.-%, in each case based on the total weight of the glass. A preferred aluminosilicate glass has a content of $B_2O_3$ of less than 8 wt.-%, preferably at maximum 7 wt.-%, particularly preferably in a range from 0 to 7 wt.-%, in each case based on the total weight of the glass. For the use in this document, a borosilicate glass is a glass which has a content of $B_2O_3$ of at least 1 wt.-%, preferably at least 2 wt.-%, more preferably at least 3 wt.-%, more preferably at least 4 wt.-%, even more preferably at least 5 wt.-%, particularly preferable in a range from 5 to 15 wt.-%, in each case based on the total weight of the glass. A preferred borosilicate glass has a content of $Al_2O_3$ of less than 7.5 wt.-%, preferably less than 6.5 wt.-%, particularly preferably in a range from 0 to 5.5 wt.-%, in each case based on the total weight of the glass. In a further aspect, the borosilicate glass has a content of $Al_2O_3$ in a range from 3 to 7.5 wt.-%, preferably in a range from 4 to 6 wt.-%, in each case based on the total weight of the glass.

A glass which is further preferred according to the invention is essentially free from B. Therein, the wording "essentially free from B" refers to glasses which are free from B which has been added to the glass composition by purpose. This means that B may still be present as an impurity, but preferably at a proportion of not more than 0.1 wt.-%, more preferably not more than 0.05 wt.-%, in each case based on the weight of the glass.

Pharmaceutical and Cosmetical Composition

In the context of the invention, every pharmaceutical composition and every cosmetical composition which the skilled person deems suitable comes into consideration. A pharmaceutical composition is a composition comprising at least one pharmaceutically active ingredient. A preferred pharmaceutically active ingredient is a vaccine. A cosmetical composition is a composition comprising at least one cosmetically active ingredient. A preferred cosmetically active ingredient is hyaluronic acid or botulinum toxin. The pharmaceutical or cosmetical composition may be fluid or solid or both, wherein a fluid composition is particularly preferred herein. A preferred solid composition is granular such as a powder, a multitude of tablets or a multitude of capsules. A further preferred pharmaceutical or cosmetical composition is a parenterialium, i.e., a composition which is intended to be administered via the parenteral route, which may be any route which is not enteral. Parenteral administration can be performed by injection, e.g., using a needle (usually a hypodermic needle) and a syringe, or by the insertion of an indwelling catheter.

Wall

If a wall of a container comprises one or more layers which are superimposed to one another, these layers are joined to one another. Two layers are joined to one another when their adhesion to one another goes beyond Van-der-Waals attraction forces. Unless otherwise indicated, layers may follow one another in a direction of a thickness of the wall indirectly, in other words with one or at least two intermediate components, or directly, in other words without any intermediate component. This is particularly the case with the formulation wherein one layer superimposes another. Further, if a component is superimposed onto a layer or a surface, this component may be contacted with that layer or surface or it may not be contacted with that layer or surface, but be indirectly overlaid onto that layer or surface with another component (e.g., a layer) in-between.

Alkali Metal Barrier Layer and Hydrophobic Layer

Preferably, the wall of the container is superimposed by an alkali metal barrier layer or by a hydrophobic layer or both, in each case towards the interior volume of the container, preferably across at least a part of the interior surface, more preferably the full interior surface of the wall. The alkali metal barrier layer may consist of any material or any combination of materials which the skilled person deems suitable for providing a barrier action against migration of an alkali metal ion, preferably against any alkali metal ion. The alkali metal barrier layer may be of a multilayer structure. Preferably, the alkali metal barrier layer comprises $SiO_2$, preferably a layer of $SiO_2$. Further, the hydrophobic layer may consist of any material or any combination of materials which provides a layer surface towards the interior volume which has a contact angle for wetting with water of more than 90°. The hydrophobic layer preferably allows for the formation of a well-defined cake upon freeze-drying, in particular in terms of a shape of the cake. A preferred hydrophobic layer comprises a compound of the general formula $SiO_xC_yH_z$, preferably a layer of this compound. Therein, x is a number which is less than 1, preferably in a range from 0.6 to 0.9, more preferably from 0.7 to 0.8; y is a number in a range from 1.2 to 3.3, preferably from 1.5 to 2.5; and z is a number as well.

Measurement Methods

The following measurement methods are to be used in the context of the invention. Unless otherwise specified, the measurements have to be carried out at an ambient temperature of 23° C., an ambient air pressure of 100 kPa (0.986 atm) and a relative atmospheric humidity of 50%.

Wall Thickness and Tolerance of Wall Thickness

The wall thickness and deviations from the mean value of the wall thickness (tolerance) are determined in accordance with the following standards for the respective type of container: DIN ISO 8362-1 for vials, DIN ISO 9187-1 for ampoules, DIN ISO 110 4 0-4 for syringes, DIN ISO 13926-1 for cylindrical cartridges, and DIN ISO 11040-1 for dental cartridges.

The invention is set out in more detail below by means of examples and figures, with the examples and figures not denoting any restriction on the invention. Furthermore, unless otherwise indicated, the figures are not to scale.

For each of the examples and comparative examples 16 containers are loaded into a holding device, also referred to as a nest. Therein, the containers are commercially available glass vials of the type SCHOTT Type I Plus® from Schott AG and of size 100R according to the standard DIN ISO 8362-1:2016-06. From top to bottom, each of the vials includes a flange, a neck in form of a hollow cylinder, a rounded shoulder, a body region in form of a hollow cylinder, a rounded heel and a bottom region which is a standing bottom. The flange and the neck allow to apply a lid by crimping.

The following nests are used. Each of these nests includes 4 rows and, perpendicular thereto, 4 columns of openings for holding vials. Accordingly, each of the nests, used in the examples and comparative examples, is configured for holding 16 vials.

Comparative Example 1 (not According to the Invention)

For the comparative example 1, so called clip-nests as described below in the context of FIG. 18 are used.

Comparative Example 2 (not According to the Invention)

For the comparative example 2, so called cup-nests as described below in the context of FIG. 19 are used.

Example 1 (According to the Invention)

For the example 1, nests of the type shown in FIGS. 1 and 2 are used. FIG. 3 shows a section through a loaded nest of this type.

Example 2 (According to the Invention)

For the example 2, nests of the type shown in FIGS. 6 and 7 are used. FIG. 8 shows a section through a loaded nest of this type.

Example 3 (According to the Invention)

For the example 3, nests of the type shown in FIGS. 10 and 11 are used. FIG. 12 shows a section through a loaded nest of this type.

Each of the loaded nests of the examples and comparative examples may be placed in a tub as depicted in FIG. 14. The filled tub may be closed by sealing a lid onto the upper rim of the tub.

In the TABLE 1, ++ indicates a result which is more favourable than +, which is more favourable than 0, which is more favourable than –, which is still more favourable than – –.

TABLE 1

|  | Accessibility of Vial Bottom | Accessibility of Vial Body Region | Accessibility of Vial Top Region | Reusability of holding Device | Suitability for Recycling | Complexity of Production |
|---|---|---|---|---|---|---|
| Comparative Example 1 | + | — | — | — | + | + |
| Comparative Example 2 | — | — | ++ | ++ | + | + |

TABLE 1-continued

|  | Accessibility of Vial Bottom | Accessibility of Vial Body Region | Accessibility of Vial Top Region | Reusability of holding Device | Suitability for Recycling | Complexity of Production |
|---|---|---|---|---|---|---|
| Example 1 | + | + | + | + | + | + |
| Example 2 | + | + | + | 0 | + | + |
| Example 3 | + | + | + | ++ | — | — |

As discussed above, the shelf life of many pharmaceuticals can be increased rather gently and conveniently by the process of lyophilization. This process requires the vial bottom to be accessible from below. The summary in the above TABLE 1 shows that the bottoms of the vials loaded into the nests of comparative example 1 or examples 1 to 3 are easily accessible from below. In result, the vials can easily be lyophilised while being held by any of these nests. In the nest of comparative example 2, the bottoms of the vials are not or at least far less conveniently accessible from below. It follows that the nests of the comparative example 1 and examples 1 to 3 are well suited for filling vials which are held in these nests with an aqueous pharmaceutical or cosmetical composition and lyophilising the composition in the vials while they are being held by the nest. On the other hand, if a nest according to comparative example 2 is used, the vials have to be removed from this nest for lyophilization. Accordingly, an additional holder is needed for holding the vials during the lyophilization process.

Further, the cylindrical body regions of the vials, held in the nests of the examples 1 to 3 are better assessible than those of the vials held by the nests of the comparative examples. Of course, the cup-nest of comparative 2 covers at least wide parts of the body region of the vials held therein. Further, the clips of the nest of comparative example 1 have to protrude above the carrier plate of the nest. In consequence, the carrier plate has to be at a rather low position with respect to the height of the vials. Accordingly, the carrier plate blocks a part of the body region of each of the vials. In the nests of the examples 1 to 3, the holding elements do not protrude above the carrier plate of the respective nest. Therefore, the carrier plate can be arranged at a higher position with respect to the height of the vials. In consequence, the carrier plate covers a smaller or no part of the body region of each vial. In essence, the body regions of vials held in the nests of the examples 1 to 3 are better accessible than those of vials held in the cup- and clip-nests. The vial body region has to be accessible for irradiation with X-rays or gamma rays or for contact with steam or hydrogen peroxide in order to sterilise the vials. This means that the nests of the examples 1 to 3 allow to more efficiently and more conveniently sterilise vials which are held in these nests.

Furthermore, for applying lids to the vial openings by crimping, the flanges and necks of the vials have to be accessible from above. Of course, in the nest of comparative example 2, the top regions of the vials are most easily accessible. However, in regard of this criterion the nests of the examples 1 to 3 are still far more convenient than the clip-nest of comparative example 1.

In summary, only the nests of the examples 1 to 3 allow to thoroughly sterilise the vials held in these nests, to fill the vials with an aqueous pharmaceutical or cosmetical composition, to conveniently lyophilise the composition in the vials, and to close the vials by crimping while the vials are still held by the nests. Hence, the vials can be transported to the pharmaceutical company in a nest according to any of the examples 1 to 3. Here, the nest may be packaged in a tub of the type shown in FIG. 14. This tub may be further packaged in a plastic bag. At the pharmaceutical company, the nest can be unpackaged from the bag and the tub. Then the vials can be processed in the nest until the vials are ready to be packaged for retail.

Further, in the field of pharmaceutical packaging, often disposable packagings are used. Accordingly, a lot of plastic waste is generated. In view of the sustainability criterion, reusability of packaging is an issue. After having opened and closed the clips of the nest of comparative example 1 a number of times, there will be fatigue of material and the clips will eventually break. This limits reusability of the clip-nests. The holding elements of the nests of the examples 1 to 3 are less prone to suffer from fatigue and break, even when being reused a large number of times. Therefore, those nests can be reused many times. This holds in particular for the holding elements according to example 3. Needless to say, that the cup-nests of comparative example 2 can also be reused many times. This renders the nests of the comparative example 2 and the examples 1 to 3 advantageous over the clip-nets of example 1 in terms of sustainability.

If reusing the nest does not come into consideration or at the end of its reusability the nest has to be disposed of. Here, the sustainability criterion calls for the nest to be as easy as possible recyclable. In terms of suitability for recycling, the nests of the examples 1 and 2 are superior over the nest of example 3. Separating the different materials of the holding elements of the nest according to example 3 turns out to be rather cumbersome if not reasonably impossible. Further, production of the holding elements of example 3 is more complex and lengthy than production of the holding elements of the nests according to the other examples.

BRIEF DESCRIPTION OF THE DRAWINGS

FIG. 9a shows a schematic section of a detail of the arrangement of FIG. 8;

FIG. 9b shows a further schematic section of a detail of the arrangement of FIG. 8;

FIG. 10 shows a schematic view of a further holding device according to the invention from above;

FIG. 13a shows a schematic top view onto an opening of the holding device of FIG. 10 with its holding element;

FIG. 13b shows a schematic section of a detail of the arrangement of FIG. 12;

FIG. 14 shows a partial view of a further arrangement according to the invention;

FIG. 15 shows a flow chart of a process of the invention for loading and packaging a plurality of containers;

FIG. 16 shows a scheme of an apparatus of the invention;

DETAILED DESCRIPTION

Figure 1:
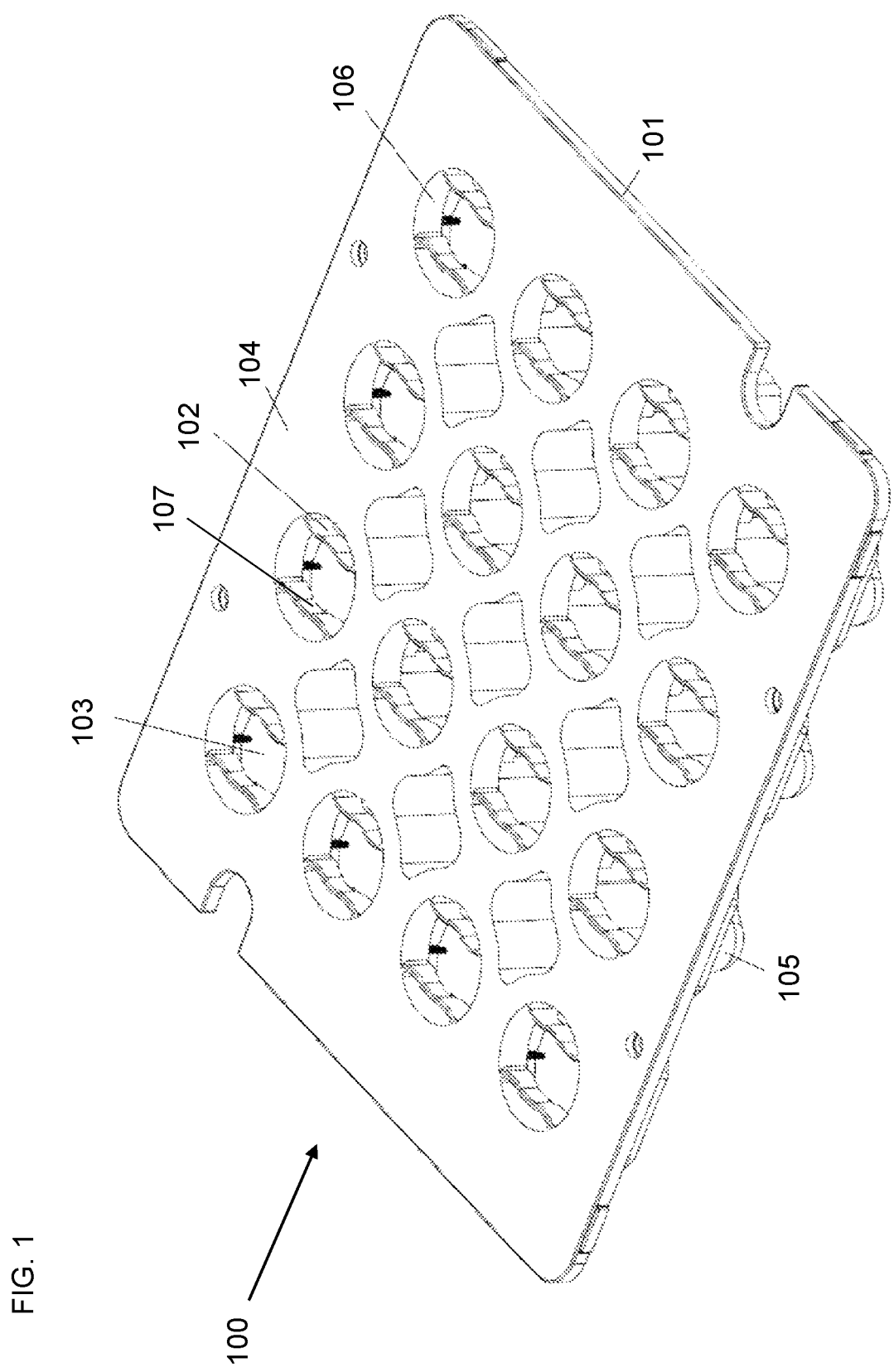
FIG. 1 shows a schematic view of a holding device according to the invention from above.

FIG. 1 shows a schematic view of a holding device 100 according to the invention from above. This holding device 100 comprises a plate-like base body 101 (also referred to as carrier plat), made from polypropylene, and a plurality of holding elements 102 which are arranged at the base body 101. The base body 101 comprises a plurality openings 103 in a first surface 201 (not to be seen in FIG. 1, see FIG. 2), which is opposite to a further surface 104 of the base body. The first 201 and further surfaces 104 are plane-parallel to each other. The openings 103 are cylindrical through-holes which extend through the base body 101 from the first surface 201 to the further surface 104. Accordingly, a lateral surface 106 of each of the openings 103 is a cylinder shell surface. Further, the openings 103 are arranged regularly in rows and columns which are perpendicular to one another and which each contain 4 of the openings 103. Accordingly, there are altogether 16 openings 103. In each of the openings 103, two holding elements 102 are arranged. The two holding elements 102, which are arranged in a respective opening 0103, do not protrude from this opening 103, neither beyond the first surface 201, nor beyond the further surface 104. For each opening 103, the two holding elements 102 are designed and arranged to hold a container 301 (not shown in FIG. 1, see FIG. 3), which extends via the first 201 and further surfaces 104 through this opening 103, by in a positive fit. In a direction which is perpendicular to a height of this container 301 a movable surface 107 of each of the two holding elements 102 faces the container 301. The holding device 100 is designed and arranged such that establishing the positive fit includes displacing each of the two the movable surfaces 107 by a translational displacement movement 404). A direction of the displacement movement 404 is perpendicular to the height of the container 301 and, at the same time, approximately parallel to the first 201 and further surfaces 104. The holding device 100 further comprises a plurality of spacer elements 105, which can be seen better in the view from below shown in FIG. 2. The holding elements 102 are made from a flexible material such as an elastomer, for example a silicone, so that they can be displaced between a basic configuration and a widened insertion configuration, in which a distance between the two holding elements 102 of an opening 103 is larger than a maximum outer diameter of the container 301 to be held, thus enabling insertion of the container 301 into the opening 103 from vertically above or below the holding device 100.

Figure 2:
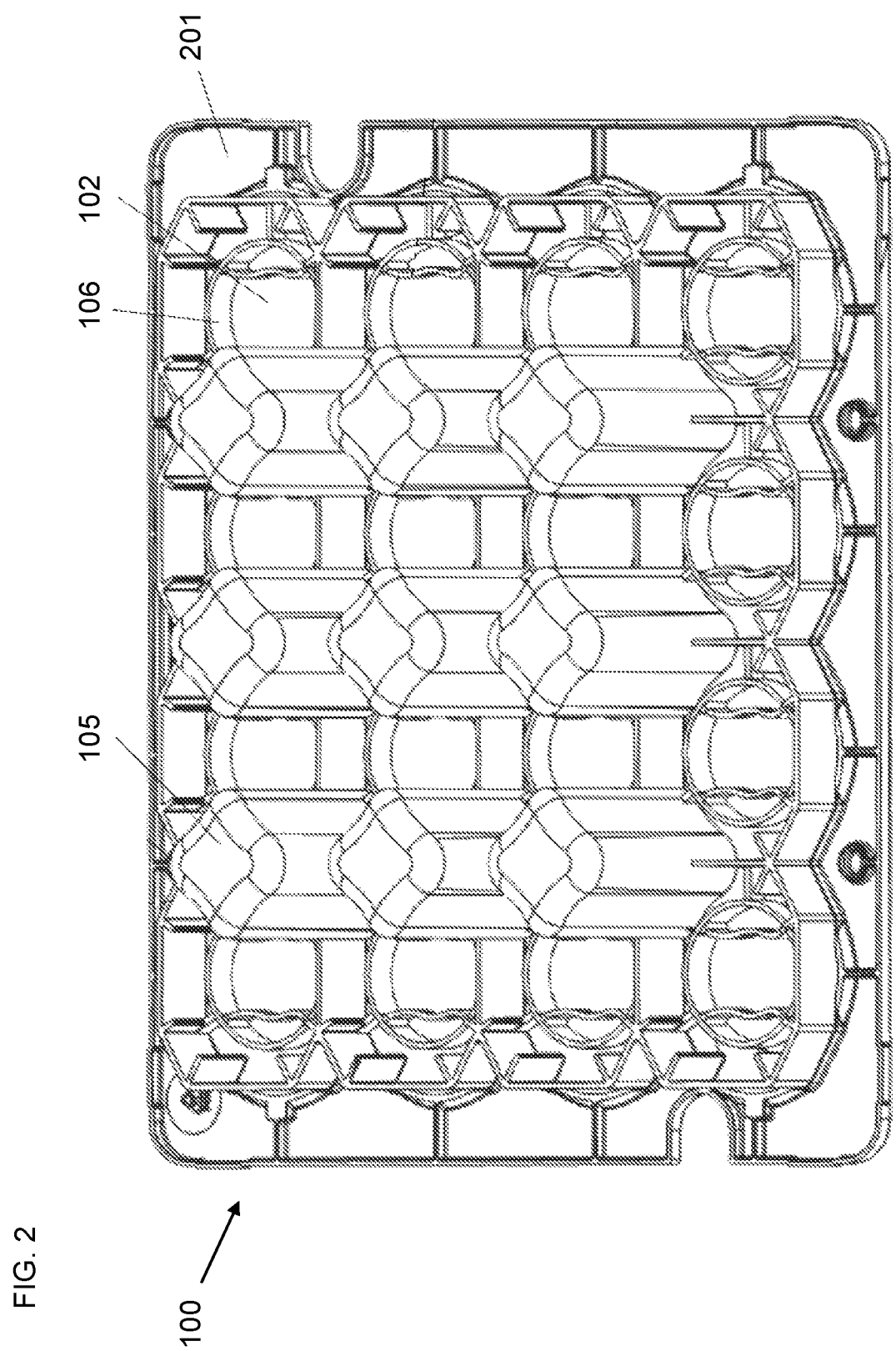
FIG. 2 shows a schematic view of the holding device according to the invention of FIG. 1 from below.

FIG. 2 shows a schematic view of the holding device 100 according to the invention of FIG. 1 from below. What can be seen is that the spacer elements 105 are arranged at the first surface 201 and each of the spacer elements 105 protrudes from the first surface 201 away from the base body 101 by 10 cm. On a side of the first surface 201 which faces away from the base body 101, between each two neighboring openings 103 of the plurality of openings 103, there is arranged at least part of a spacer element 105.

Figure 3:
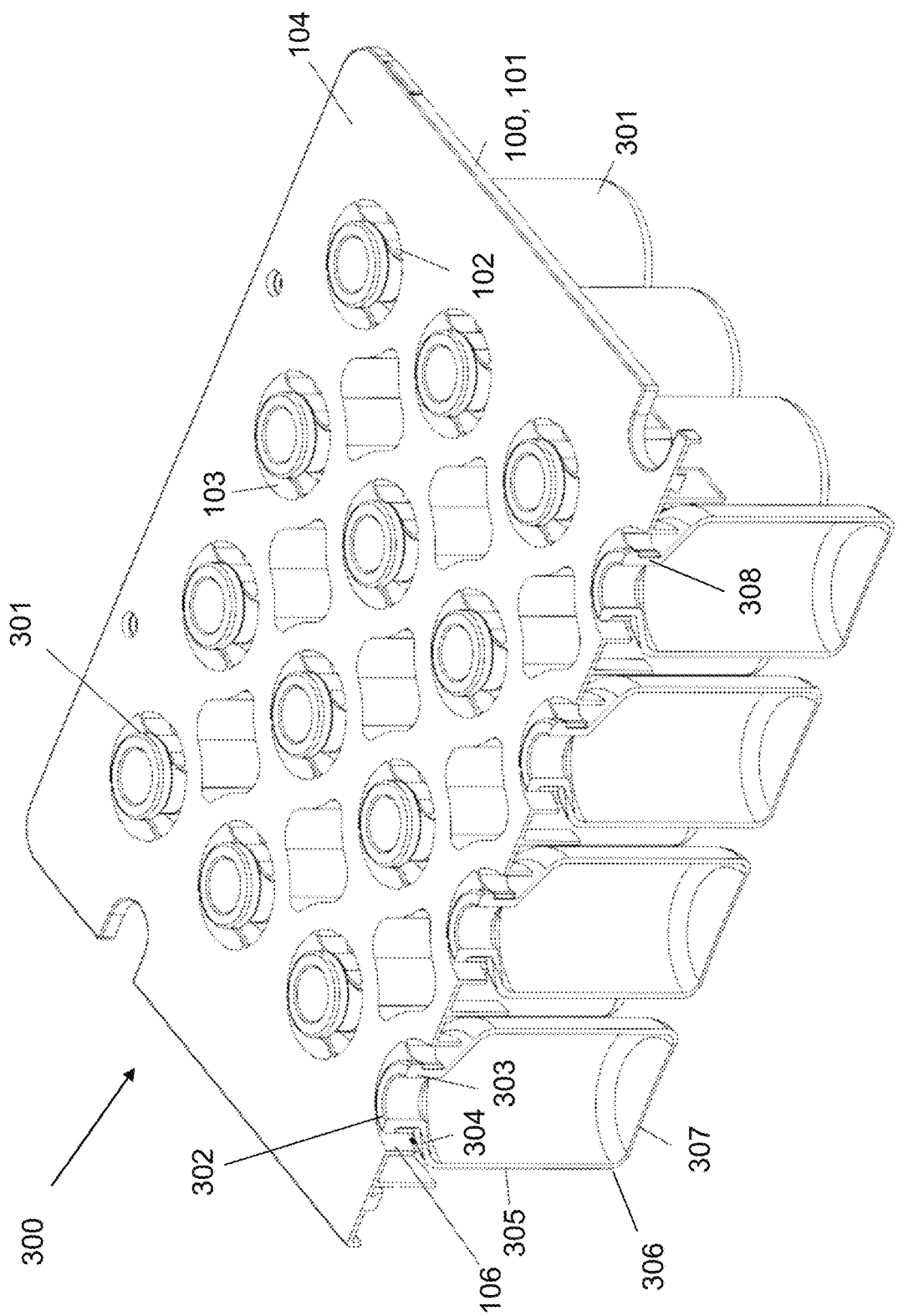
FIG. 3 shows a schematic section of an arrangement according to the invention.

FIG. 3 shows a schematic section of an arrangement 300 according to the invention. The arrangement 300 comprises the holding device 100 of FIGS. 1 and 2 and a plurality of containers 301. The containers 301 are pharmaceutical packaging vials of the type SCHOTT Type I Plus® from Schott AG and of size 100R according to the standard DIN ISO 8362-1:2016-06. Accordingly, each of the containers 301 comprises a wall of glass, which, except for a container opening, encloses an interior volume. The wall of glass of each container 301 consists from top to bottom of the container 301 of a top region, which consists of a flange 302 and a neck 303; followed by a shoulder 304 and a body region 305; followed by a heel 306 and a bottom region 307. The body region 305 as well as the neck 303 are of cylindrical shape. The holding region 308 of a respective container 301 is a region of an outer surface of the neck 303 of this container 301. Each of the containers 301 of the plurality of containers 301 extends via an opening 103 of the plurality of openings 103 through the first surface 201 and the further surface 104 of the base body 101 of the holding device 100. Further, each of the containers 301 is held in a positive fit by two holding elements 102 of the respective opening 103. Therein, the movable surfaces 107 of the two holding elements 102 face a holding region 308 of the outer surface of the container 301. The holding region 308 of the container 301 is part of the outer surface of the neck 303 of the respective container 301.

Figure 4:
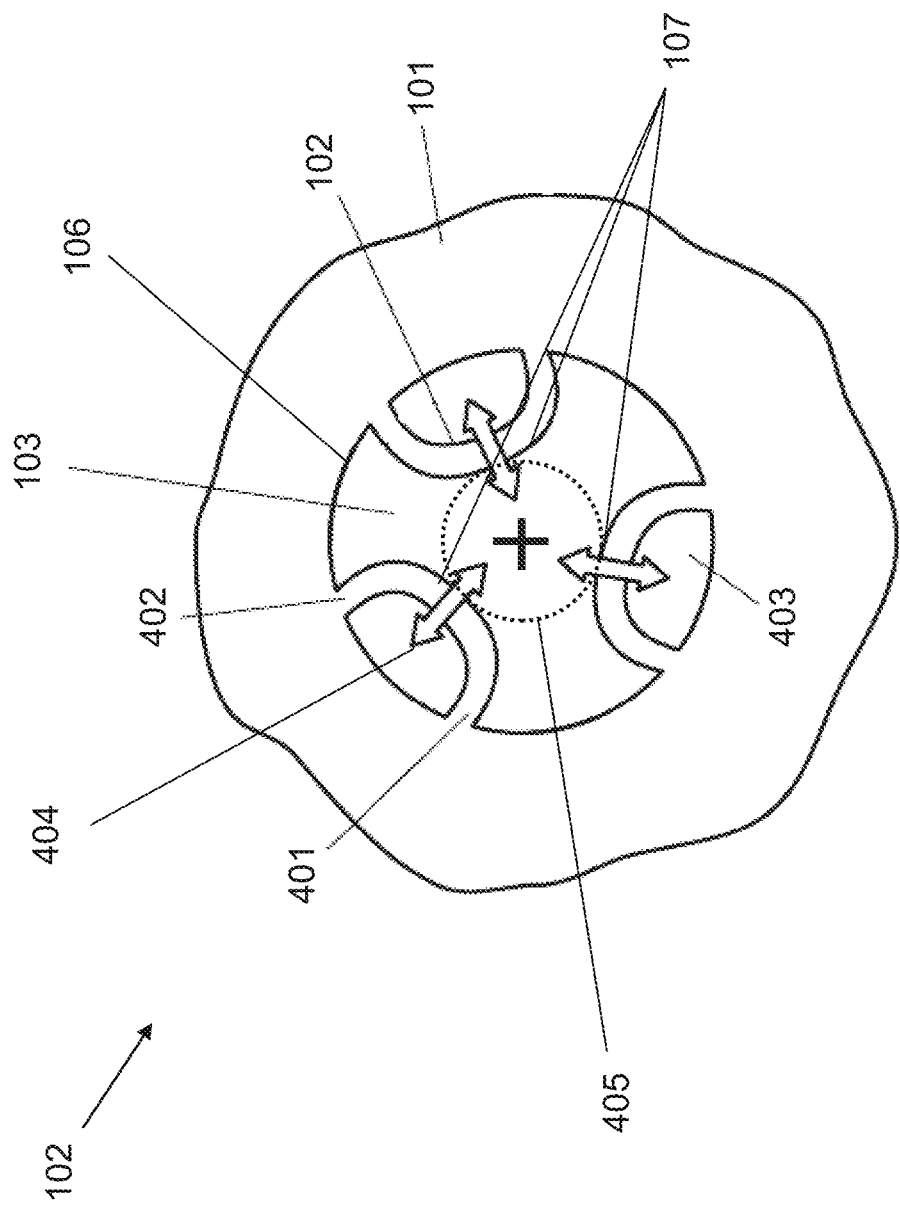
FIG. 4 shows a scheme of an opening of the holding device of FIG. 1 with its holding elements.

FIG. 4 shows a scheme of an opening 103 of the holding device 100 of FIG. 1 with its two holding elements 102. What can be seen is that, the holding elements 102 are ribbon-shaped. Within a plane in the opening 103, which is the plane of the FIG. 4, each of the two holding elements 102 extends from a starting point 401 to an end point 402, wherein the starting point 401 and the end point 402 are at a lateral surface 106 of the opening 103. Within the preceding plane, there is a gap 403 between each of the two holding elements 102 and a circumference of the opening 103. Establishing the positive fit between the holding elements 102 and the container 301 includes elastically deforming the holding elements 102 such that the movable surfaces 107 are displaced by the displacement movement 404 which is depicted by arrows in the figure. A direction of the displacement movement 404 is perpendicular to a height of the container 301, based on the container 301 being held in the positive fit. Further, the direction of the displacement movement 404 is parallel to the first 201 and further surfaces 104 as well as to the plane of the FIG. 4. The movable surfaces 107 partially enclose a holding area 405. Here, a ratio of the holding area 405 to a total opening area of the opening 103 is about 0.12.

Figure 5:
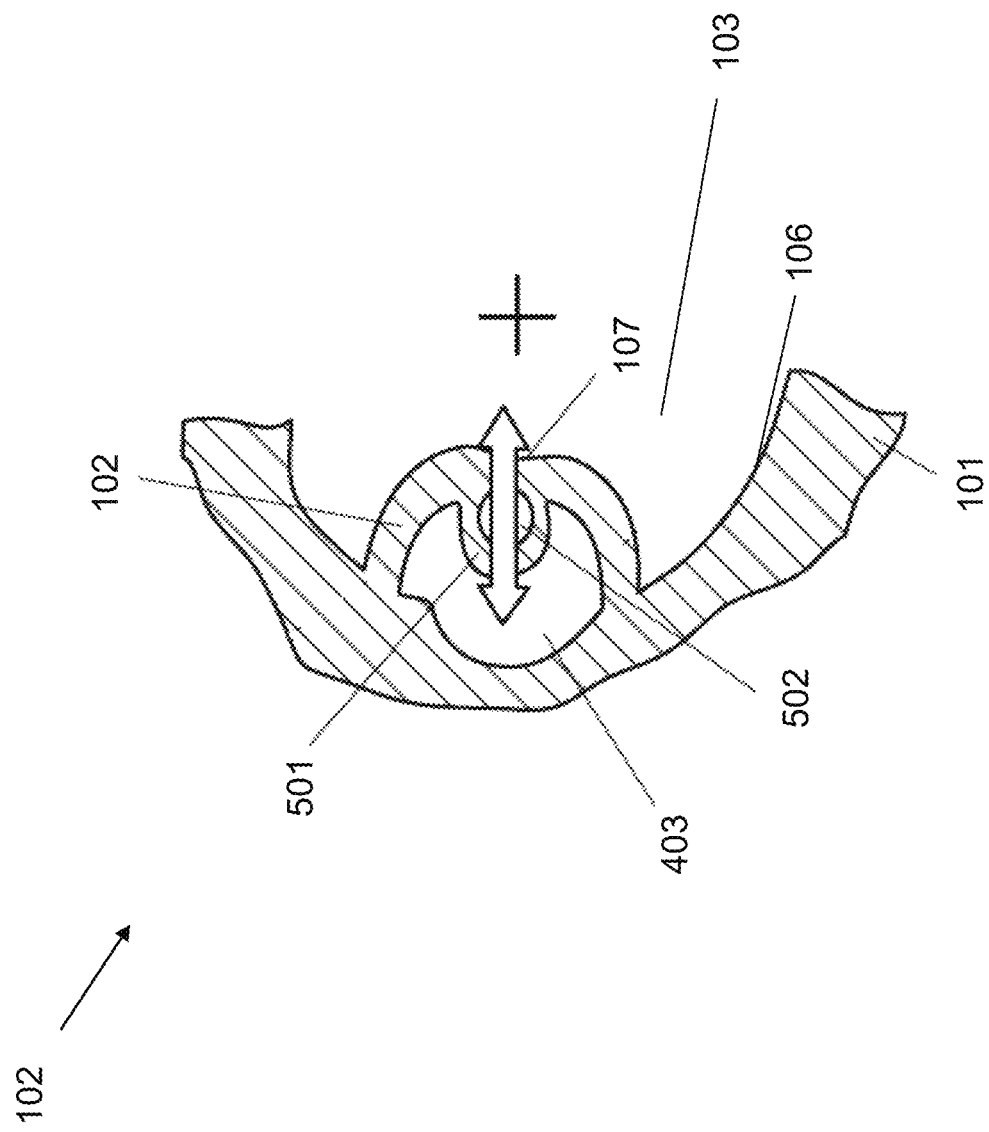
FIG. 5 shows a scheme of a detail of a holding element of a holding device according to the invention.

FIG. 5 shows a scheme of a detail of a holding element 102 of a further holding device 102 according to the invention. What can be seen is that this holding element 102 is ribbon-shaped. Further, there is a gap 403 between the holding element 102 and a circumference of the opening 103. Furthermore, an actuating flap 501 is formed on a side of the holding element 102 facing the lateral surface 106 of the opening 103. The actuating flap 501 allows to easily apply an actuating tool to a hole 502 for actuating the displacement movement 404 of the holding element 102 for insertion of a container 301 into the opening 103 or removal thereof.

Figure 6:
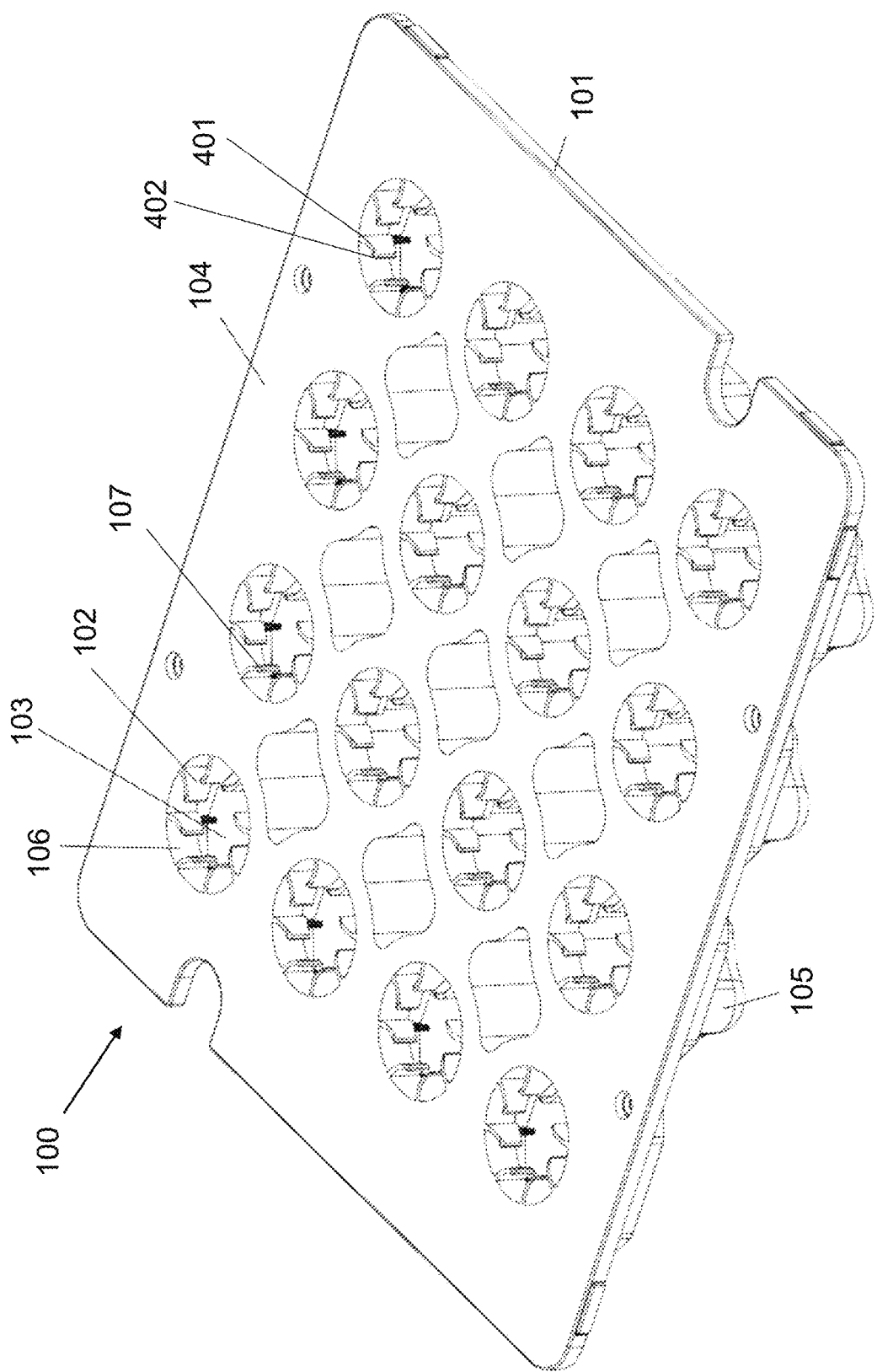
FIG. 6 shows a schematic view of a further holding device according to the invention from above.

FIG. 6 shows a schematic view of a further holding device 100 according to the invention from above. The holding device 100 of FIG. 6 is identical to the holding device 100 of FIG. 1, except for the holding elements 102. In FIG. 6, each of the openings 103 comprises 6 holding elements 102 which do not protrude from the opening 103, they are arranged in. Within a plane in the respective opening 103, each of the 6 holding elements 102 in this opening 103 extends curvilinearly from its starting point 4001 to its end point 402, wherein the end point 402 is closer to a center of an opening area of the opening 103 than the starting point 401. This way, the 6 holding elements 102 of each opening form a holding structure of an iris diaphragm type. The holding elements 102 are made from a flexible material, such as an elastomer.

Figure 7:
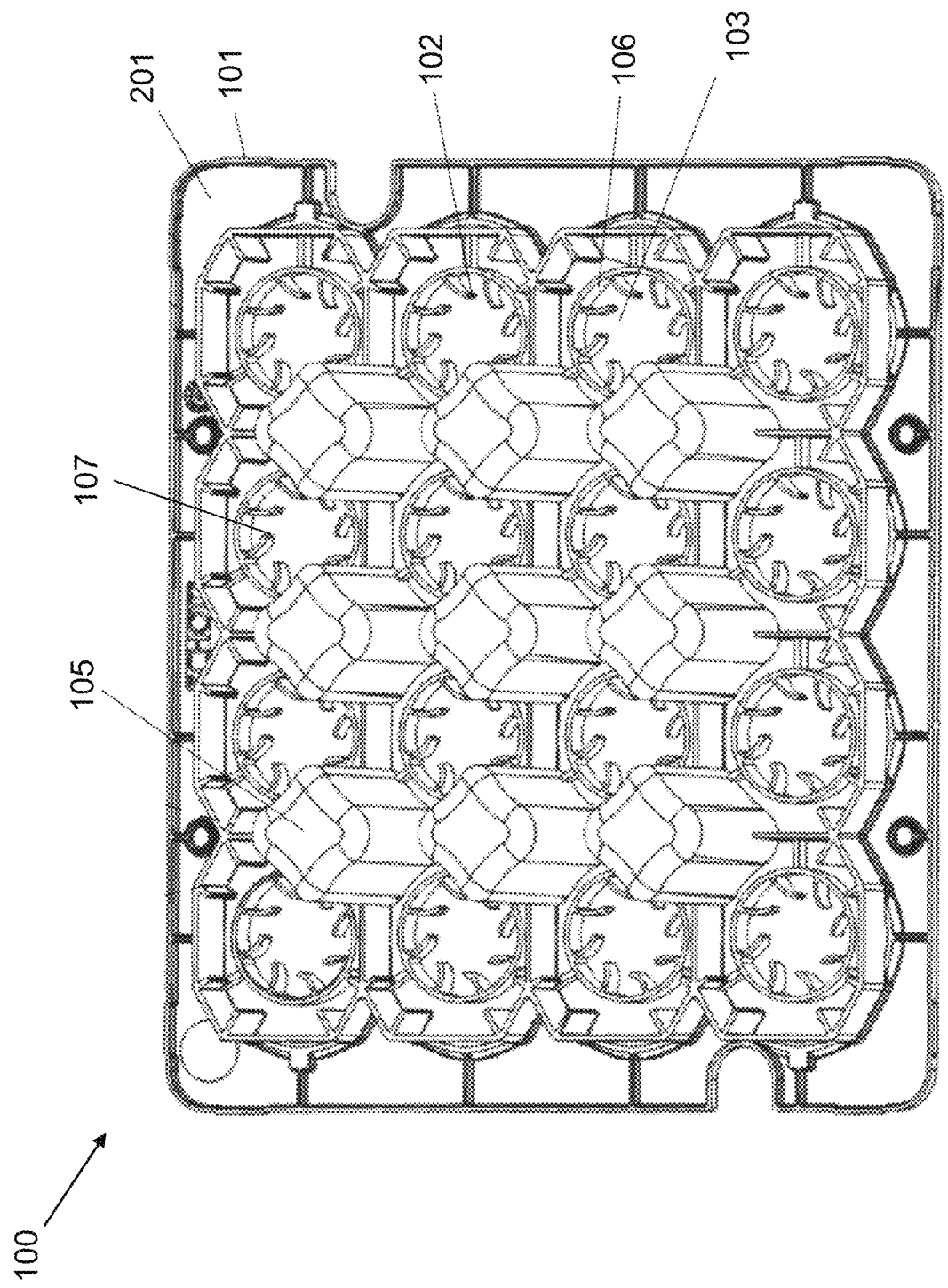
FIG. 7 shows a schematic view of the holding device according to the invention of FIG. 6 from below.

FIG. 7 shows a schematic view of the holding device 100 according to the invention of FIG. 6 from below.

Figure 8:
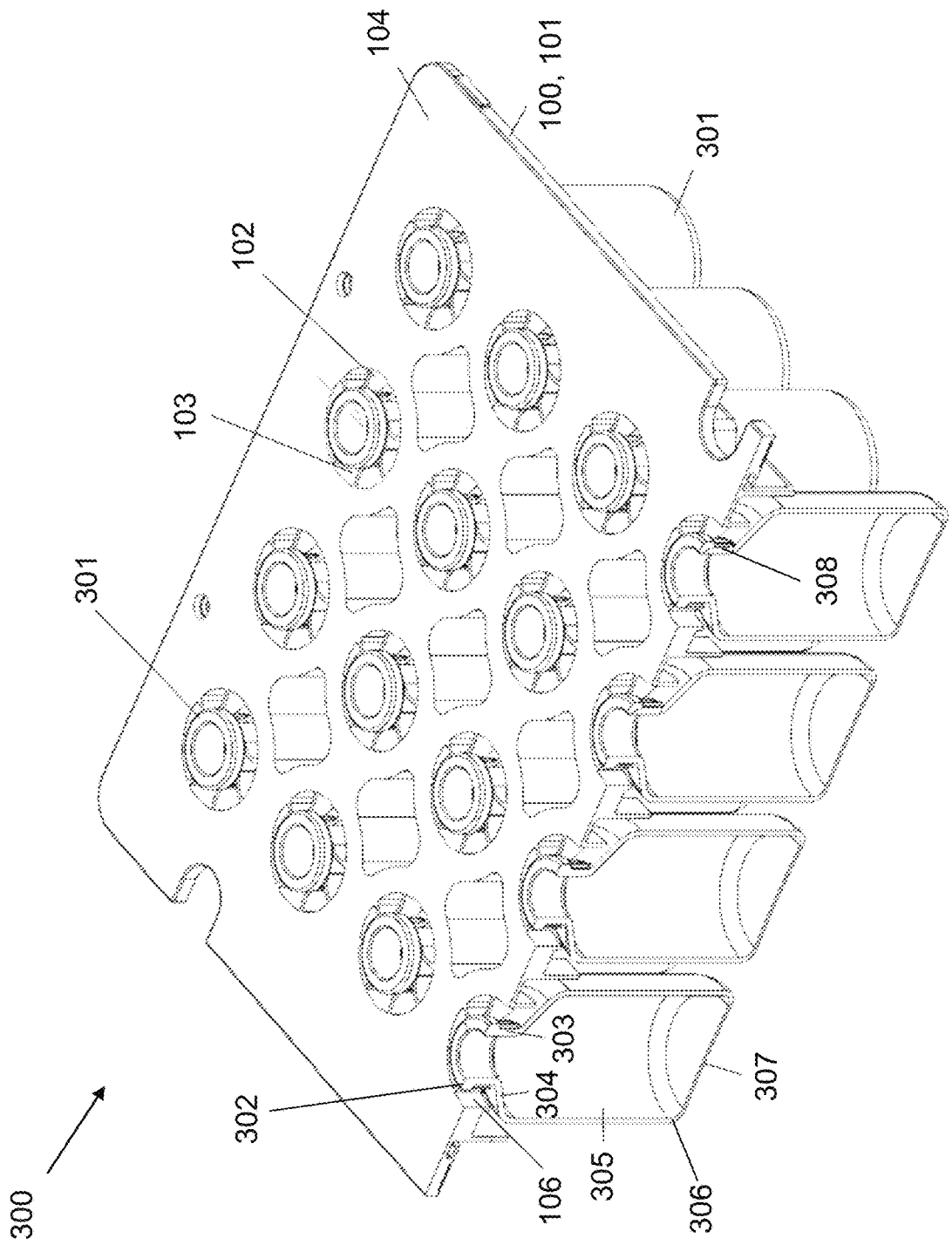
FIG. 8 shows a schematic section of a further arrangement according to the invention.

FIG. 8 shows a schematic section of a further arrangement 300 according to the invention. The arrangement 300 comprises the holding device 100 of FIGS. 6 and 7 and a plurality of containers 301. The containers 301 are the vials described in the context of FIG. 3. Each of the containers 301 of the plurality of containers 301 extends via an opening 103 of the plurality of openings 103 through the first surface 201 and the further surface 104 of the base body 101 of the holding device 100. Further, each of the containers 301 is held in a positive fit between the movable surfaces 107 of the 6 holding elements 102 in the respective opening 103 and the container 301. Therein, the movable surfaces 107 of the 6 holding elements 102 face a holding region 308 of the outer surface of the container 301 neck 303.

FIG. 9a shows a schematic section of a detail of the arrangement 300 of FIG. 8. What is shown is a longitudinal section through one of the containers 301 which is held by the holding device 100 of the arrangement 300.

FIG. 9b shows a further schematic section of a detail of the arrangement 300 of FIG. 8. This figure, as well, is a longitudinal section through one of the containers 301 which is held by the holding device 100 of the arrangement 300. Deviating from FIGS. 8 and 9a, the neck 303 of the container 301, shown in FIG. 9b, is not of cylindrical shape. This is to emphasise that the holding device 100 of the invention is also suitable for holding containers 301, the holding regions 308 of which are not cylinder shell surfaces. Here, a ratio of a height H2 of the movable surfaces 107 to a height H1 of the holding region 308 of the container 301 is 0.9.

FIG. 10 shows a schematic view of a further holding device 100 according to the invention from above. The holding device 100 of FIG. 10 is identical to the holding device 100 of FIG. 1, except for the holding elements 102. In FIG. 10, each of the openings 103 comprises exactly one holding element 102 which does not protrude from the opening 103, which it is arranged in. Details of the holding elements 102 of the holding device 100 of FIG. 10 can be seen in FIGS. 12, 13a and b).

Figure 11:
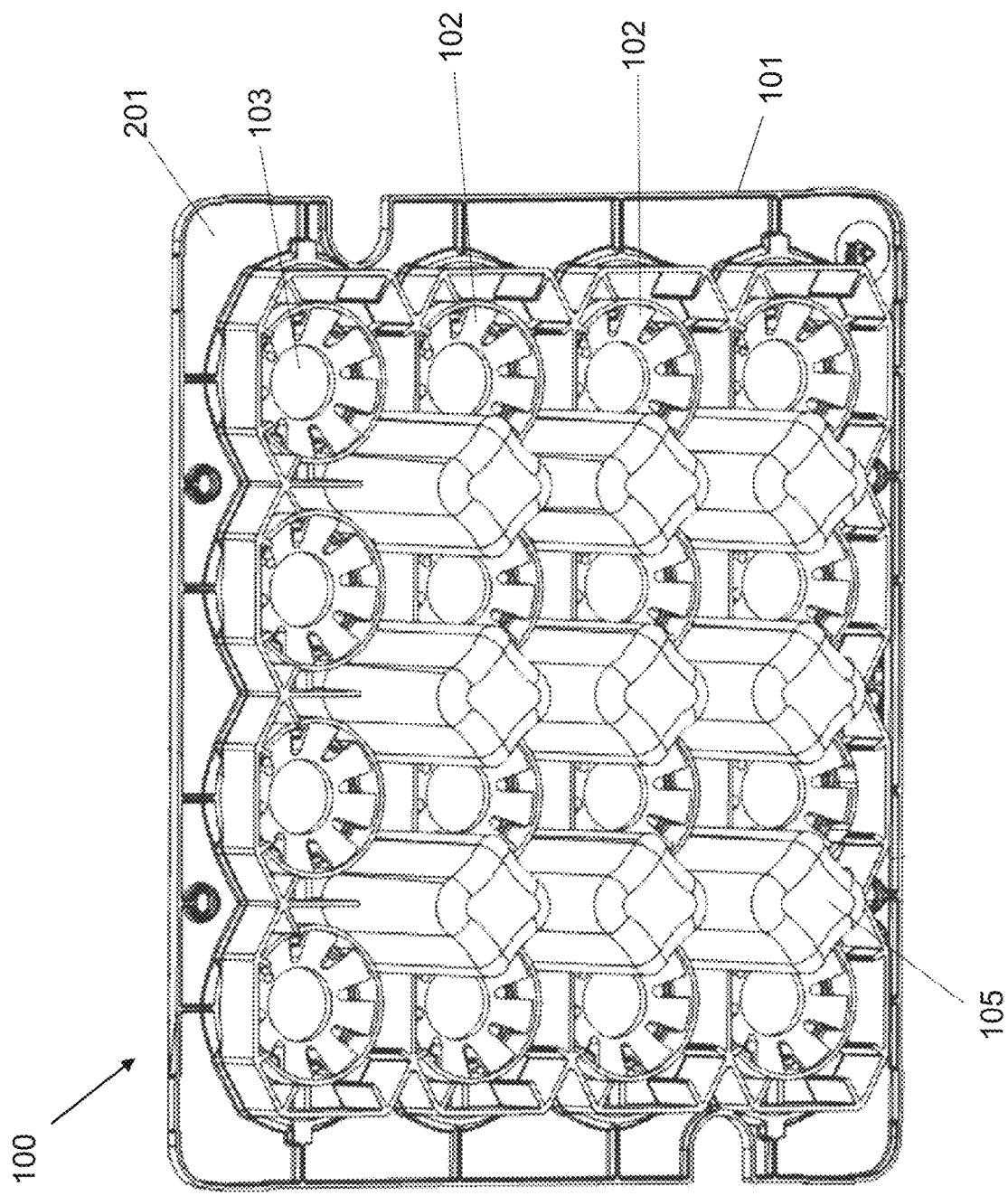
FIG. 11 shows a schematic view of the holding device according to the invention of FIG. 10 from below.

FIG. 11 shows a schematic view of the holding device 100 according to the invention of FIG. 10 from below.

Figure 12:
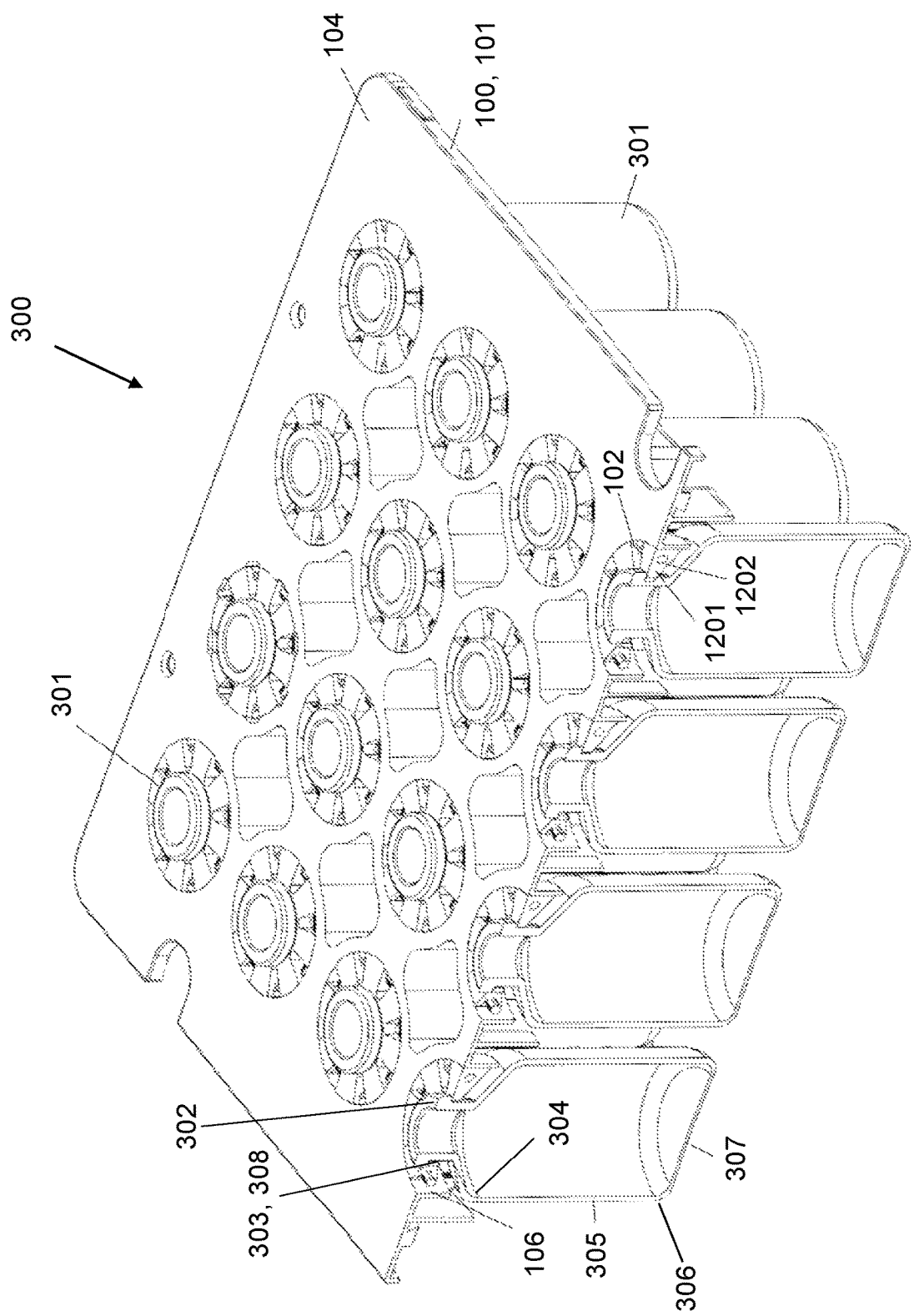
FIG. 12 shows a schematic section of a further arrangement according to the invention.

FIG. 12 shows a schematic section of a further arrangement 300 according to the invention. The arrangement 300 comprises the holding device of FIGS. 10 and 11 and a plurality of containers 301. The containers 301 are the vials described in the context of FIG. 3. Each of the containers 301 of the plurality of containers 301 extends via an opening 103 of the plurality of openings 103 through the first surface 201 and the further surface 104 of the base body 101 of the holding device 100. Further, each of the containers 301 is held in a positive fit between the holding element 102 of the respective opening 103 and the container 301. Therein, the movable surface 107 of the holding element 102 faces a holding region 308 of the outer surface of the container 301 neck 303. What can be seen from the holding elements 102 shown in section in FIG. 12 is that each of the holding elements 102 consists of a first part 1201 and a second part 1202. The first part 1201 is made from a thermoset 1201 which is harder than a thermoplastic elastomer 1202 which the second part 1202 is made of.

FIG. 13a shows a schematic top view onto an opening 103 of the holding device 100 of FIG. 10 with its holding element 102. It can be seen that the movable surface 107 of the holding element 102 is a cylinder shell surface formed by the second part 1202. The second part 1202 comprises a first subpart 1203 and a further subpart 1204, wherein the first part 1201 is between the first subpart 1203 and the further subpart 1204. The first subpart 1203 is of a shape of a continuous ring, whereas the further subpart 1204 is of a shape of a discontinuous ring.

FIG. 13b shows a schematic section of a detail of the arrangement 300 of FIG. 12. Here, it can be seen that the first part 1201 is embedded in the second part 1202. Further, a ratio of a height H2 of the movable surface 107 to a height H1 of the holding region 308 of the container 301 is 0.9.

FIG. 14 shows a partial view of a further arrangement 300 according to the invention. The arrangement 300 of FIG. 14 comprises the arrangement 300 of FIG. 3 and a packaging container 1401 which is a tub prepared by deep drawing. The holding device 100 and the containers 301 are arranged in the packaging container 1401 such that the first surface 201 of the holding device 100 is supported by a step 1402 of the tub 1401. Further, the tub 1401 may be closed by sealing a lid to a rim 1403.

FIG. 15 shows a flow chart of a process 1500 of the invention for loading a plurality of containers 301 into a holding device 100, and packaging the holding device 100 and the containers 301. In a step (a) 1501 of the process 1500, the holding device 100 of FIGS. 5 and 6 as well as 16 containers 301 of type described in the context of FIG. 3 are provided. In a subsequent step (b) 1502, each of the containers 301 is inserted into one of the openings 103 of the holding device 100, respectively, so that it extends through the opening 103 via the first 201 and further 104 surfaces of the base body 101 of the holding device 100. Therein, the 6 holding elements 102 of the respective opening 103 are converted from their basic configuration to their insertion configuration by displacing the movable surfaces 107 of the 6 holding elements by a displacement movement 404 which is parallel to the first 201 and further surfaces 104 and perpendicular to the height of the container 301. Once the containers 301 have been inserted, the 6 holding elements 102 are converted back into their basic configuration. In result, each of the 16 containers 301 is held in a positive fit between the 6 holding elements 102 and the container 301. Accordingly, the arrangement 300 of FIG. 8 is obtained. In a further step (c) 1503, the holding device 100 with the 16 containers 301 is placed into a packaging container 1401 which is a tub 1401. In a subsequent step (d) 1504, the packaging container 1401 is closed by sealing a lid to a rim 1403 of the tub 1401. In a further step (e) 1505 of the process 1500, the closed packaging container 1401 is placed into an outer packaging which is a plastic pouch. Subsequently, in a step (f) 1506, the outer packaging is closed by heat sealing.

FIG. 16 shows a scheme of an apparatus 1600 of the invention. This apparatus 1600 comprises a holding device feed 1601, a container feed 1602, and a loading station 1603 as components. The holding device feed 1601 is designed and arranged to feed the holding device 100 of any of FIGS. 1 and 2 to the loading station 1603. The container feed 1602 is designed and arranged to feed a plurality of the containers 301 described in the context of FIG. 3 to the loading station 1603. Here, the holding device feed 1601 and the container feed 1602 are each configured as conveyor belts. The loading station 1603 is designed and arranged to insert each of the containers 301, which have been provided by the container feed 1602, into one of the openings 103 of the holding device 100 so that each container 301 is held by the holding device 100 as shown in FIG. 3. For this purpose, the loading station 1603 comprises a robotic arm 1604. The apparatus 1600 is designed for preparing the arrangement 300 of FIG. 3.

Figure 17:
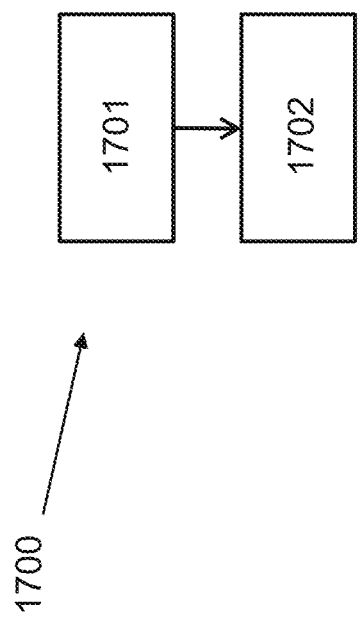
FIG. 17 shows a flow chart of a process of the invention for filling a plurality of containers with a pharmaceutical composition.

FIG. 17 shows a flow chart of a process 1700 of the invention for filling a plurality of containers 301 with a pharmaceutical composition. A process step (a) 1701 includes providing the arrangement of FIG. 3, whereas a subsequent process step (b) 1702 includes filling at least part of the containers 301 held by the holding device 100 with a vaccine.

Figure 18:
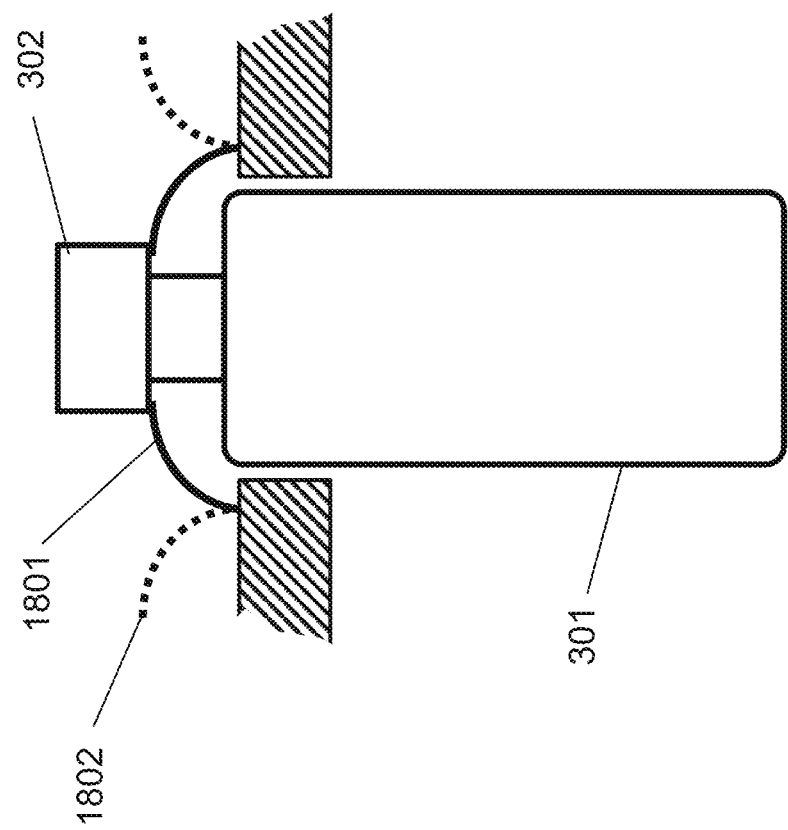
FIG. 18 shows a scheme of a detail of a clip-nest of the prior art.

FIG. 18 shows a scheme of a detail of a clip-nest of the prior art. The clip-nest includes filigree resilient holding arms, referred to as clips. FIG. 18 shows clips in a holding configuration (full lines). The broken lines show these clips in an opened configuration. The clips can be snapped from the holding configuration to the opened configuration by elastically deforming the clips. This deformation of the clips includes a swivel movement. Therein, a free end of the respective clip rotates about the other end of the clip which is attached to the carrier plate of the nest. Accordingly, this movement is not a translational movement.

Figure 19:
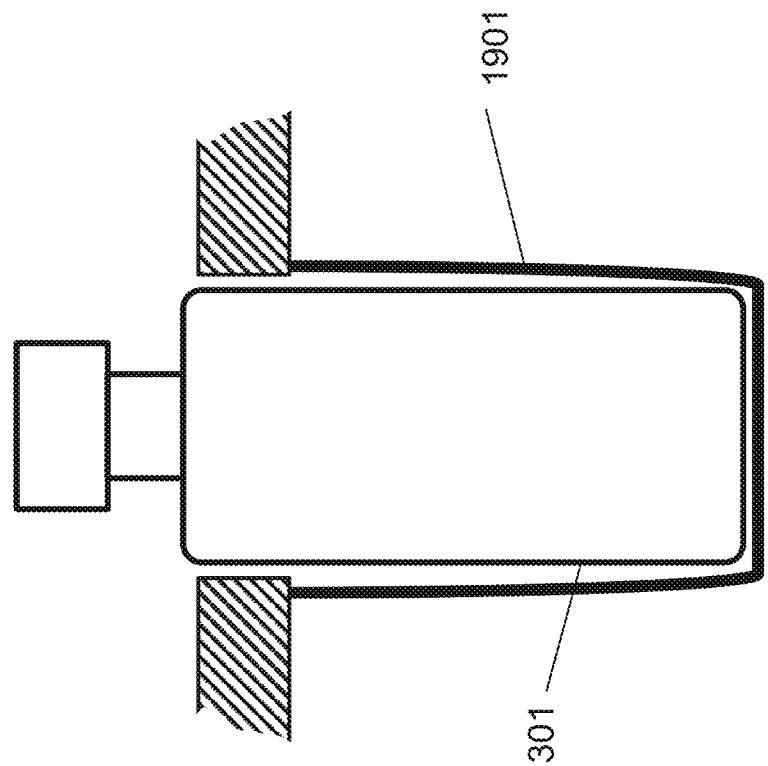
FIG. 19 shows a scheme of a detail of a cup-nest of the prior art.

FIG. 19 shows a scheme of a detail of a cup-nest of the prior art. At each opening of the nest, a receptable, referred to as cup 1901, is arranged. The containers 301 can only be placed into the cup 1901 from above the nest. Held by the nest, the containers 301 are not accessible from below. Further, if the nest is turned upside-down, the containers 301 will fall out.

LIST OF REFERENCE NUMERALS 100 holding device according to the invention
101 base body
102 holding element
103 Opening
104 further surface
105 spacer element
106 lateral surface of opening
107 movable surface
201 first surface
300 arrangement according to the invention
301 container
302 Flange
303 Neck
304 Shoulder
305 body region
306 Heel
307 bottom region
308 holding region
401 starting point
402 end point
403 Gap
404 displacement movement
405 holding area
501 actuating flap
502 hole for applying actuating tool
1201 first part/thermoset
1202 second part/thermoplastic elastomer
1203 first subpart
1204 further subpart
1301 gap between container and lateral surface of opening
1401 packaging container/tub
1402 Step
1403 rim for attaching lid
1500 process according to the invention
1501 process step (a)
1502 process step (b)
1503 process step (c)
1504 process step (d)
1505 process step (e)
1506 process step (f)
1601 holding device feed
1602 container feed
1603 loading station
1604 robotic arm
1700 process of the invention for filling containers
1701 process step (a)
1702 process step (b)
1801 closed clip
1802 opened clip
1902 cup
H1 height of holding region
H2 height of movable surface

What is claimed is:

1. A holding device comprising:
a base body having a plurality of openings in a first surface; and
a plurality of holding elements each having a movable surface, the plurality of holding elements being arranged with respect to the plurality of openings, respectively, such that a container having a height extending along an axis perpendicular to the first surface in a respective opening of the plurality of openings is held by a respective one of the plurality of holding elements in a positive fit,
wherein, in a direction that is perpendicular to the height of the container, the movable surface faces the container,
wherein the holding element is designed and arranged to establish the positive fit by a displacement movement of the movable surface,
wherein the displacement movement has a direction of movement that inclines an angle with the height of the container in a range from 60 to 120°, and
wherein the movable surface at least partially encloses a holding area, the holding area has a ratio to an area of the respective opening that is in a range from more than 0.01 to less than 0.95.

2. The holding device of claim 1, wherein the displacement movement is selected from a group consisting of a translational movement, a rotational movement, and any combinations thereof.

3. The holding device of claim 1, wherein the plurality of holding elements have a part that is arranged in the respective opening of the plurality of openings.

4. The holding device of claim 3, wherein the moveable surface does not protrude from the opening beyond the first surface and/or beyond a further surface that is opposite to the first surface.

5. The holding device of claim 1, wherein the movable surface of the plurality of holding elements is positioned and configured so that the displacement movement is effected by an actuating tool.

6. The holding device of claim 1, wherein the plurality of holding elements are positioned and configured to not cover the container in a top view of the container and/or a bottom view of the container.

7. The holding device of claim 1, wherein the plurality of openings and the plurality of holding elements are configured so that the container is a packaging container for a pharmaceutical composition and/or a cosmetical composition.

8. The holding device of claim 1, wherein the plurality of openings and the plurality of holding elements are configured so that the container is selected from a group consisting of a vial, a syringe, a cartridge, an autoinjector, an ampoule, and any combinations thereof.

9. The holding device of claim 1, wherein the movable surface faces a holding region of the container.

10. The holding device of claim 1, wherein the holding element is designed and arranged to establish the positive fit with a container having an outer diameter in a range from 5 to 100 mm.

11. The holding device of claim 1, wherein the angle is in a range from 88 to 92°.

12. The holding device of claim 1, wherein the first surface extends in a direction of a width and a length of the base body.

13. The holding device of claim 1, wherein the holding device is sterile.

14. The holding device of claim 1, wherein the direction of the displacement movement lies in a plane that is perpendicular to the height of the container.

15. The holding device of claim 1, wherein the first surface is a planar surface.

16. The holding device of claim 1, further comprising a further surface opposite the first surface, wherein the first surface and the further surface are planar and are planparallel to one another.

17. The holding device of claim 1, further comprising a plurality of containers, a respective container of the plurality of containers extending in the respective opening of the plurality of openings and held by the respective one of the plurality of holding elements in the positive fit.

18. An arrangement comprising:
a plurality of containers having a height;
a holding element including a base body having a plurality of openings in a first surface and a plurality of holding elements each having a movable surface, the plurality of holding elements being arranged with respect to the plurality of openings, respectively, such that a container of the plurality of containers has the height extending along an axis perpendicular to the first surface in a respective opening of the plurality of openings is held by a respective one of the plurality of holding elements in a positive fit;
a packaging container, the holding element with the plurality of containers being in the packaging container; and
a lid and an outer packaging, wherein the lid is joined onto the packaging container closing the packaging container, and the outer packaging encloses the packaging container,
wherein, in a direction that is perpendicular to the height of the container, the movable surface faces the container,
wherein the holding element is designed and arranged to establish the positive fit by a displacement movement of the movable surface,
wherein the displacement movement has a direction of movement that inclines an angle with the height of the container in a range from 60 to 120°.

* * * * *